(12) United States Patent
Cheng

(10) Patent No.: US 12,329,475 B2
(45) Date of Patent: Jun. 17, 2025

(54) INVERSE KINEMATIC CONTROL SYSTEMS FOR ROBOTIC SURGICAL SYSTEM

(71) Applicant: Covidien LP, Mansfield, MA (US)

(72) Inventor: Jiqi Cheng, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 422 days.

(21) Appl. No.: 17/857,364

(22) Filed: Jul. 5, 2022

(65) Prior Publication Data

US 2022/0338943 A1   Oct. 27, 2022

Related U.S. Application Data

(63) Continuation of application No. 16/081,773, filed as application No. PCT/US2017/020567 on Mar. 3, 2017, now abandoned.

(60) Provisional application No. 62/303,437, filed on Mar. 4, 2016.

(51) Int. Cl.
| | |
|---|---|
| *A61B 34/30* | (2016.01) |
| *A61B 17/29* | (2006.01) |
| *A61B 34/00* | (2016.01) |
| *B25J 9/16* | (2006.01) |
| *B25J 13/02* | (2006.01) |

(52) U.S. Cl.
CPC .............. *A61B 34/30* (2016.02); *A61B 17/29* (2013.01); *A61B 34/74* (2016.02); *A61B 34/76* (2016.02); *B25J 9/1689* (2013.01); *B25J 13/025* (2013.01)

(58) Field of Classification Search
CPC ......... A61B 34/30; A61B 17/29; A61B 34/37; A61B 34/74; A61B 34/76; B25J 13/025; B25J 9/1689; B25J 9/1607; B25J 9/1697
See application file for complete search history.

(56) References Cited

U.S. PATENT DOCUMENTS

| | | |
|---|---|---|
| 6,132,368 A | 10/2000 | Cooper |
| 6,206,903 B1 | 3/2001 | Ramans |
| 6,246,200 B1 | 6/2001 | Blumenkranz et al. |

(Continued)

FOREIGN PATENT DOCUMENTS

WO   2017151996 A1   9/2017

OTHER PUBLICATIONS

Examination Report issued in corresponding application EP 17 760 865.0 dated Aug. 25, 2023 (5 pages).

(Continued)

*Primary Examiner* — Scott Luan

(74) *Attorney, Agent, or Firm* — Carter, DeLuca & Farrell LLP

(57) ABSTRACT

A method of using inverse kinematics to control a robotic system includes receiving an input pose from a user interface to move an arm of the robotic system, calculating a remote center of motion for a desired pose from the input pose in a tool center-point frame, checking when the desire pose needs correction, correcting the desired pose of the arm, and moving the am to the desired pose in response to the input pose. The am of the robotic system including a tool having a jaw disposed at an end of the arm. Checking when the desired pose needs correction includes verifying that the remote center of motion is at or beyond a boundary distance in the desired pose. Correcting the desired pose of the arm occurs when the remote center of motion is within the boundary distance.

16 Claims, 17 Drawing Sheets

(56) References Cited

U.S. PATENT DOCUMENTS

| | | |
|---|---|---|
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |

(56) References Cited

U.S. PATENT DOCUMENTS

| | | |
|---|---|---|
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |

(56) References Cited

U.S. PATENT DOCUMENTS

| | | |
|---|---|---|
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2003/0029463 A1* | 2/2003 | Niemeyer ............ H04N 13/239 348/E13.016 |
| 2008/0215065 A1 | 9/2008 | Wang et al. |
| 2011/0028992 A1 | 2/2011 | Geiger et al. |
| 2011/0257661 A1 | 10/2011 | Choi et al. |
| 2012/0059391 A1 | 3/2012 | Diolaiti et al. |
| 2013/0325032 A1 | 12/2013 | Schena et al. |
| 2015/0202015 A1 | 7/2015 | Elhawary et al. |

OTHER PUBLICATIONS

International Search Report dated Jul. 11, 2017 issued in PCT/US2017/020567.

John Craig, "Introduction to Robotics: Mechanics and Control", Prentice Hall; 3rd edition (Aug. 6, 2004).

Hamidreza Azimian, "Preoperative Planning of Robotics-Assisted Minimally Invasive Cardiac Surgery Under Uncertainty", Ph.D thesis, The University of Western Ontario, 2012.

H. Mayer, I. Nagy, and A. Kroll, "Inverse Kimematics of a Manipulator for Minimally Invasive Surgery," Technischen Universitat Munchen, Tech, Rep. TUM-10404, Jan. 2004.

Extended European Search Report dated Oct. 11, 2019 corresponding to counterpart Patent Application EP 17760865.0.

Chinese First Office Action dated Nov. 11, 2020 corresponding to counterpart Patent Application CN 201780014961.

Indian Office Action dated May 10, 2021 corresponding to counterpart Patent Application IN 201817029176.

* cited by examiner

INVERSE KINEMATIC CONTROL SYSTEMS FOR ROBOTIC SURGICAL SYSTEM

CROSS-REFERENCE TO RELATED APPLICATIONS

This application is a continuation of U.S. patent application Ser. No. 16/081,773, filed Aug. 31, 2018, which is a U.S. National Stage Application filed under 35 U.S.C. § 371(a) of International Patent Application Serial No. PCT/US2017/020567, filed Mar. 3, 2017, which claims the benefit of and priority to U.S. Provisional Patent Application Ser. No. 62/303,437, filed Mar. 4, 2016, the entire disclosure of which is incorporated by reference herein.

BACKGROUND

Robotic surgical systems such as teleoperative systems are used to perform minimally invasive surgical procedures that offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a stapler, an electrosurgical instrument, etc., in response to movement of input devices by a surgeon viewing images captured by the image capturing device of a surgical site. During a surgical procedure, each of the tools is inserted through an opening, either natural or an incision, into the patient and positioned to manipulate tissue at a surgical site. The openings are placed about the patient's body so that the surgical instruments may be used to cooperatively perform the surgical procedure and the image capturing device may view the surgical site.

During the surgical procedure, the tools are manipulated in multiple degrees of freedom. When one or more of the degrees of freedom align with one another a singularity is created. As the tool approaches a singularity, the operation of the tool may become unpredictable and the degrees of freedom of the tool may be decreased. To prevent the tool from reaching a singularity, some systems employ hard stops. Other systems allow the tool to reach a singularity and use a comparison of a speed of an input controller with a speed of movement of the tool to predict the movement of the tool.

There is a continuing need to control a tool of a robotic surgical system as the tool approaches and/or passes through a singularity. Additionally or alternatively, there is a need to control a tool of a robotic surgical system to avoid reaching a singularity and to maintain each degree of freedom of the tool.

SUMMARY

This disclosure relates generally to correcting the pose of an arm and a tool of a robotic system to avoid singularities between joints and to maintain degrees of freedom of movement of the arm and the tool. Specifically, when a remote center of motion of the arm is within a boundary distance from an origin of a tool center-point frame, the remote center of motion is moved to the boundary distance while maintaining a position of a jaw axis of the tool and rotating the remote center of motion according to the rigid body kinematics. After the rotation, the tool center-point frame is expressed in the rotated remote center of motion frame, and treated as the corrected desired pose for inverse kinematics calculation.

In an aspect of the present disclosure, a method of using inverse kinematics to control a robotic system includes receiving an input pose from a user interface to move an arm of the robotic system, calculating a remote center of motion for a desired pose from the input pose in a tool center-point frame, checking when the desire pose needs correction, correcting the desired pose of the arm, and moving the arm to the desired pose in response to the input pose. The arm of the robotic system includes a tool having a jaw disposed at an end of the arm. Checking when the desired pose needs correction includes verifying that the remote center of motion is at or beyond a boundary distance in the desired pose. Correcting the desired pose of the arm occurs when the remote center of motion is within the boundary distance.

In aspects, during correcting the desired pose of the arm, the jaw axis is held in position. Correcting the desired pose of the arm may include moving the remote center of motion to the boundary distance.

In some aspects, determining the boundary distance occurs as a function of a maximum joint angler of a pitch joint defined between the tool and the distance between the origin of the tool center-point and the pitch joint. The maximum joint angle of the pitch joint may be about 75°. Determining the boundary distance may include taking the sum of the distance between the origin of the tool center-point and the pitch joint and the cosine of the maximum joint angle of the pitch point. The boundary distance may be taken along the jaw axis.

In certain aspects, the method includes providing feedback when the remote center of motion approaches the boundary distance in the desired pose. Providing feedback when the remote center of motion in the desired pose approaches the boundary distance may include increasing the feedback as the remote center of motion approaches the boundary distance. Increasing the feedback may include linearly or exponentially increasing the feedback. Alternatively, increasing the feedback may include linearly increasing the feedback as the remote center of motion approaches the boundary distance and exponentially increasing the feedback as the remote center of motion crosses the boundary distance.

In particular aspects, the method includes determining a check angle that is defined between the jaw axis and a vector between an origin of the tool center-point frame and the remote center of motion when the remote center of motion is within the boundary distance. The method may include providing feedback when the check angle is below a predefined extreme angle.

In another aspect of the present disclosure, a robotic surgical system includes a processing unit, a user interface, and a robotic system. The user interface is in communication with the processing unit and includes an input handle. The robotic system is in communication with the processing unit and including an arm and a tool supported at an end of the arm. The arm defines a remote center of motion and the tool defines a tool center-point frame. The arm and the tool are configured to move to a desired pose in response to an input pose of the input handle. The processing unit is configured to verify when the remote center of motion is within the boundary distance in the desired pose. The processing unit is configured to correct the desired pose when the remote center of motion is within the boundary distance.

In aspects, the processing unit is configured to verify that a check angle defined between the jaw axis and a vector defined between an origin of the tool center-point frame and the remote center of motion is below a predefined extreme angle when the remote center of motion is within the boundary distance in the desired pose. The user interface may be configured to provide feedback to a clinician when the check angle is below the predefined extreme angle. Additionally or alternatively, the input handle may be configured to provide force feedback to a clinician when the remote center of motion approaches the boundary distance in the desired pose.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
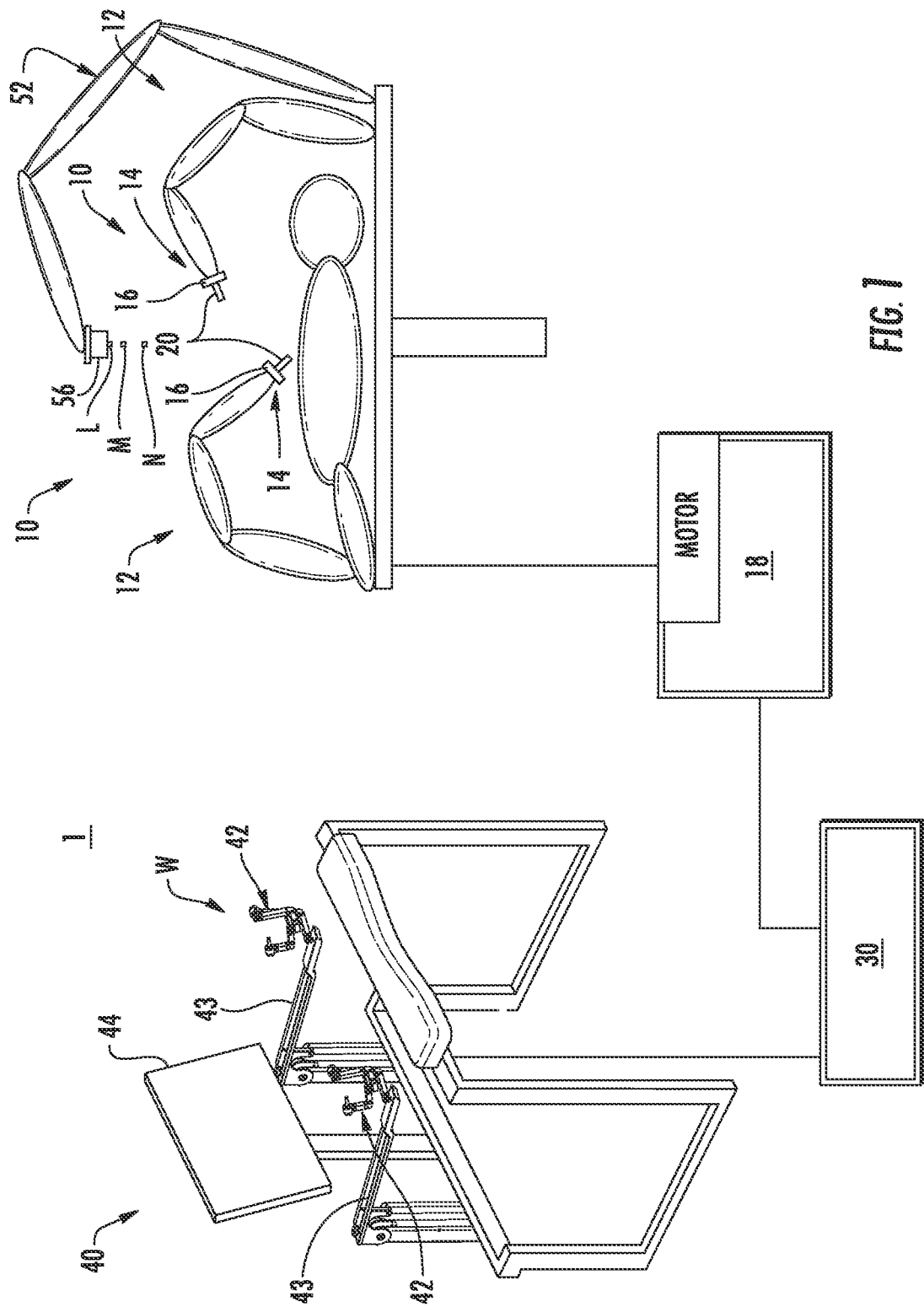
FIG. 1 is a schematic illustration of a user interface and a robotic system of a robotic surgical system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to correcting the pose of an arm and a tool of a robotic system to avoid singularities between joints and to maintain degrees of freedom of movement of the arm and the tool. Specifically, when a remote center of motion of the arm is within a boundary distance from an origin of a tool center-point frame, the remote center of motion is moved to the boundary distance while maintaining a position of a jaw axis of the tool and rotating the remote center of motion according to the rigid body kinematics. After the rotation, the tool center-point frame is expressed in the rotated remote center of motion frame, and treated as the corrected desired pose for inverse kinematics calculation.

Referring to FIG. 1, a robotic surgical system 1 in accordance with the present disclosure is shown generally as a robotic system 10, a processing unit 30, and a user interface 40. The robotic system 10 generally includes linkages or arms 12 and a robot base 18. The arms 12 moveably support an end effector or tool 20 which is configured to act on tissue. The arms 12 each have an end 14 that supports an end effector or tool 20 which is configured to act on tissue. In addition, the ends 14 of the arms 12 may include an imaging device 16 for imaging a surgical site. The user interface 40 is in communication with robot base 18 through the processing unit 30.

The user interface 40 includes a display device 44 which is configured to display three-dimensional images. The display device 44 displays three-dimensional images of the surgical site which may include data captured by imaging devices 16 positioned on the ends 14 of the arms 12 and/or include data captured by imaging devices that are positioned about the surgical theater (e.g., an imaging device positioned within the surgical site, an imaging device positioned adjacent the patient, imaging device 56 positioned at a distal end of an imaging linkage or arm 52). The imaging devices (e.g., imaging devices 16, 56) may capture visual images, infrared images, ultrasound images, X-ray images, thermal images, and/or any other known real-time images of the surgical site. The imaging devices transmit captured imaging data to the processing unit 30 which creates three-dimensional images of the surgical site in real-time from the imaging data and transmits the three-dimensional images to the display device 44 for display.

The user interface 40 also includes input handles 42 which are supported on control arms 43 which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include input devices (not shown) which allow the surgeon to manipulate (e.g., clamp, grasp, fire, open, close, rotate, thrust, slice, etc.) the tools 20 supported at the ends 14 of the arms 12.

Each of the input handles 42 is moveable through a predefined workspace to move the ends 14 of the arms 12 within a surgical site. The three-dimensional images on the display device 44 are orientated such that movement of the input handle 42 moves the ends 14 of the arms 12 as viewed on the display device 44. It will be appreciated that the orientation of the three-dimensional images on the display device may be mirrored or rotated relative to view from above the patient. In addition, it will be appreciated that the size of the three-dimensional images on the display device 44 may be scaled to be larger or smaller than the actual structures of the surgical site permitting a clinician to have a better view of structures within the surgical site. As the input handles 42 are moved, the tools 20 are moved within the surgical site as detailed below. As detailed herein, movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Figure 2:
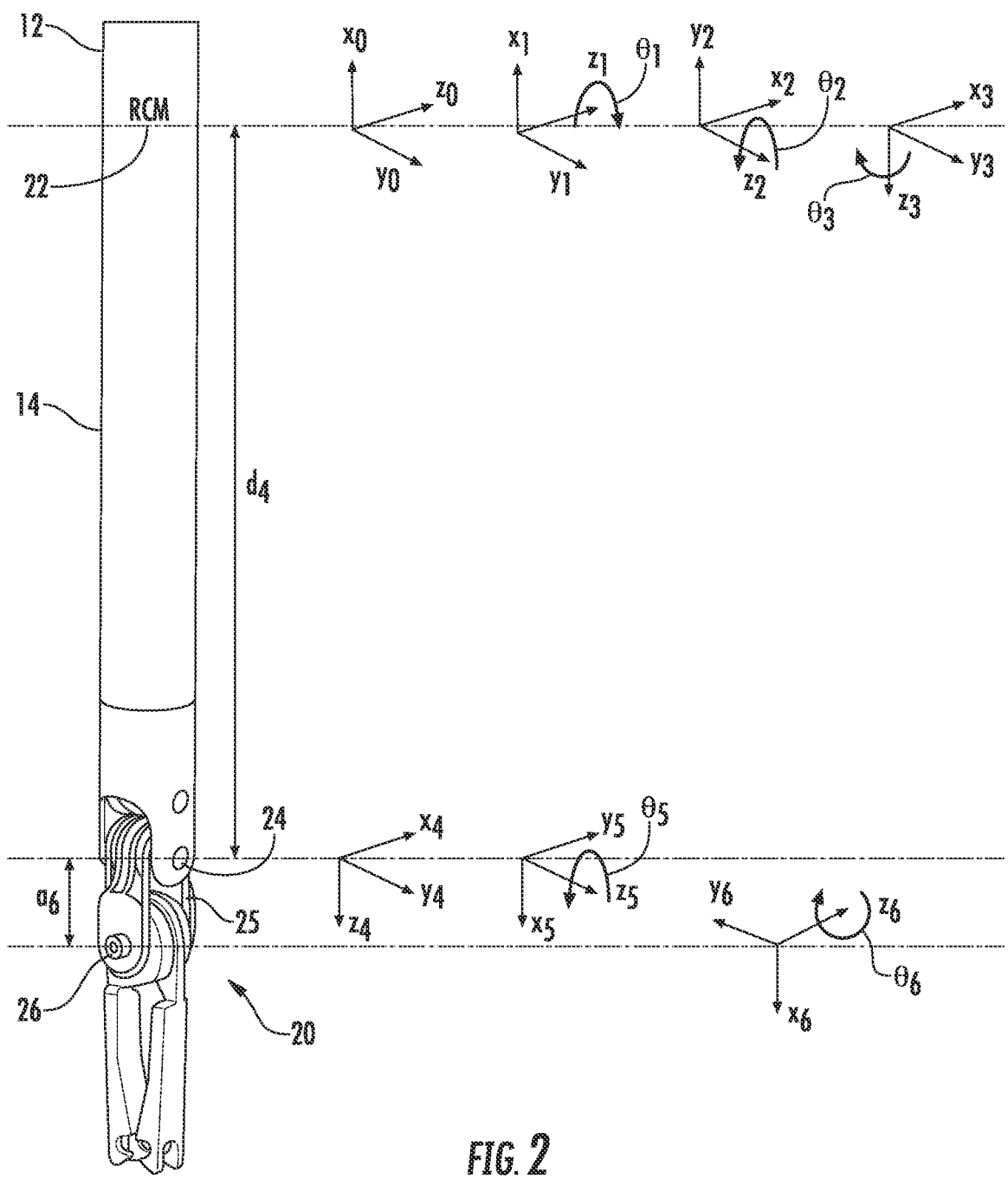
FIG. 2 is a side view of an exemplary arm and tool of the robotic system of FIG. 1.

With reference to FIG. 2, the end 14 of an arm 12 of the robotic system 10 is moveable about a Remote Center of Motion (RCM) 22 in four Degrees of Freedom (DOF) or joints. In addition, the tool 20 is pivotal in two DOF about a first tool joint 24 and a second tool joint 26, respectively. The arm 12 of the robotic system 10 defines a frame $x_0$, $y_0$, $z_0$ (the Base Frame) positioned at the RCM. The first DOF or yaw joint of the arm 12 is represented by the frame $x_1$, $y_1$, $z_1$ (Frame 1) with the position of the arm 12 about the yaw joint represented as joint angle $\theta_1$. The second DOF or pitch joint of the arm 12 is represented by the frame $x_2$, $y_2$, $z_2$ (Frame 2) with the position of the arm 12 about the pitch joint represented as joint angle $\theta_2$. The third DOF or roll joint of the arm 12 is represented by the frame $x_3$, $y_3$, $z_3$ (Frame 3) with the position of the arm 12 about the roll joint represented as joint angle $\theta_3$. The fourth DOF or linear joint is represented by the frame $x_4$, $y_4$, $z_4$ (Frame 4) and with the position of the first tool joint 24 from the RCM 22 represented as distance $d_4$. Movement of the tool 20 about the first tool joint 24 is defined in the fifth DOF or tool pitch joint represented in the frame $x_5$, $y_5$, $z_5$ (Frame 5) with the position of the tool pitch joint represented as joint angle $\theta_5$. Movement of the tool 20 about the second tool joint 26 is defined in the sixth DOF or tool yaw joint in the frame $x_6$, $y_6$, $z_6$ (Frame 6) with the position in the tool yaw joint represented as joint angle $\theta_6$. The orientation of the end effector 29 is represented by the $\hat{x}_6$ axis.

Using a typical forward kinematics model based on the frame attachments detailed above, the Denavit-Hartenberg (DH) parameters of the intracorporeal chain is shown in Table 1 below. As used herein "i" is the frame number, "a" is the length from the common normal, "α" is the angle about the common normal, "D" is the offset along previous z axis to the common normal, "θ" is the angle about previous z axis, and the joint type is the type of movement about the joint. It will be appreciated that the common normal is along the arm 12.

TABLE 1

| i | $a_{i-1}$ | $\alpha_{i-1}$ | $D_i$ | $\theta_i$ | Joint Type |
|---|---|---|---|---|---|
| 1 | 0 | 0 | 0 | $\theta_1$ | Rotational |
| 2 | 0 | $-\pi/2$ | 0 | $\theta_{2-\pi/2}$ | Rotational |

TABLE 1-continued

| i | $a_{i-1}$ | $\alpha_{i-1}$ | $D_i$ | $\theta_i$ | Joint Type |
|---|---|---|---|---|---|
| 3 | 0 | $-\pi/2$ | 0 | $\theta_3$ | Rotational |
| 4 | 0 | 0 | $d_4$ | 0 | Linear |
| 5 | 0 | $-\pi/2$ | 0 | $\theta_{5-\pi/2}$ | Rotational |
| 6 | $a_6$ | $-\pi/2$ | 0 | $\theta_6$ | Rotational |

Further, the Homogenous transform for movement in the six DOF is as follows:

$$^{i-1}_iT = \begin{bmatrix} c\theta_i & -s\theta_i & 0 & a_{i-1} \\ s\theta_i c\alpha_{i-1} & c\theta_i c\alpha_{i-1} & -s\alpha_{i-1} & -s\alpha_{i-1}d_i \\ s\theta_i s\alpha_{i-1} & c\theta_i s\alpha_{i-1} & c\alpha_{i-1} & c\alpha_{i-1}d_i \\ 0 & 0 & 0 & 1 \end{bmatrix} \quad (1)$$

where $c\theta \triangleq \cos\theta$ and $s\theta \triangleq \sin\theta$, this convention will be used throughout this disclosure. Thus, the final pose of frame 6 in the base frame 0 is defined as:

$$^0_6T = {}^0_1T\,{}^1_2T\,{}^2_3T\,{}^3_4T\,{}^4_5T\,{}^5_6T \quad (2)$$

Figure 3:
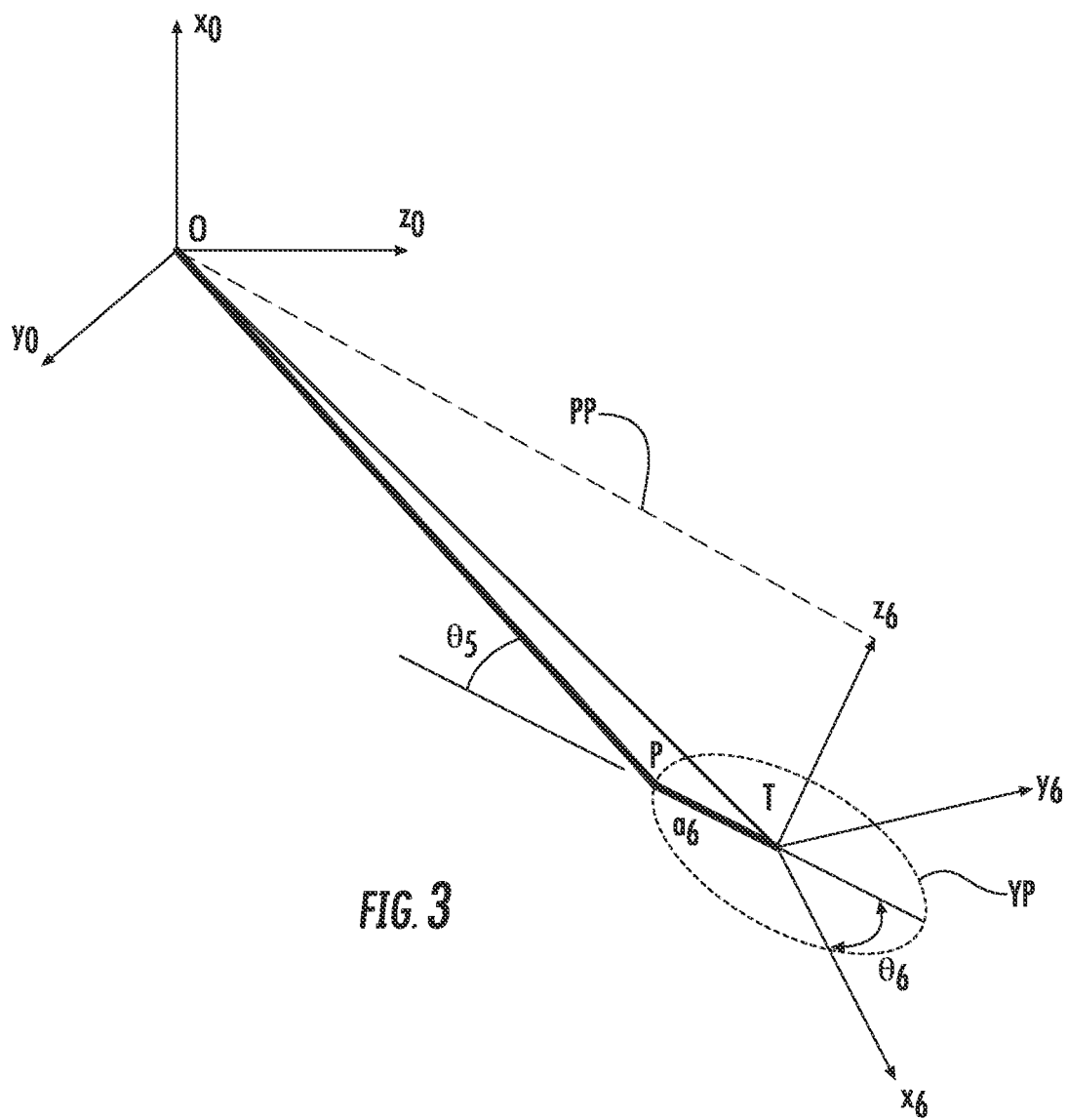
FIG. 3 is a model of the arm and tool of FIG. 2 in a first case.

With reference to FIG. 3, an inverse kinematic model for the arm 12 and the tool 20 in accordance with the present disclosure is disclosed. With reference to FIG. 3 and used in the following equations, the RCM 22 is represented by trocar point "O" and is the point at which the end 14 of the arm 12 or the tool 20 passes through a trocar (not shown) in to the body cavity of the patient. The tool pitch joint 24 is represented by point "P" and the tool yaw joint 26 is represented by yaw point "T". A yoke 25 (FIG. 2) of the tool 20 may be represented by the line "PT". In this model a frame of a jaw 29 of the tool 20 is represented by the Frame 6 and may be referred to as the tool-center-point frame (TCP frame) with the jaw direction positioned along the $\hat{x}_6$ axis. In addition, the yaw point "T" may be referred to as the "TCP" point herein.

As shown in FIG. 3, the jaw direction $\vec{T}x_6$ is known as the direction of the $\hat{x}_6$ axis. With the jaw direction $\vec{T}x_6$ fixed, the joint angle $\theta_6$ can be determined by placing the following two constraints on the pitch point "P". First, the pitch point "P" is in a yaw plane "YP" defined by rotation of the yoke "PT" around the $\hat{z}_6$ axis, shown as the dashed circle "YP" in FIG. 3, with both the yoke PT and the jaw direction $\vec{T}x_6$ lying in the yaw plane "YP". As shown, when joint angle $\theta_6$ changes, the pitch point "P" will be in the yaw plane "YP" a distance $a_6$ from the yaw point T. Second, the pitch point "P" is also in a pitch plane "PP" which is perpendicular to the yaw plane "YP" defined by the trocar point "O" and the $\hat{z}_6$ axis.

With these two constraints placed on the pitch point "P", three cases can be defined to determine the location of the pitch point "P". In the first case modeled in FIG. 3, the pitch plane "PP" is uniquely defined by the trocar point "O" and the $\hat{z}_6$ axis and intersects the yaw plane "YP" at the pitch point "P" on a proximal side (i.e., closer to the trocar point "O") of the yaw point "T". Thus, in the first case, the joint angle $\theta_6$ and the joint angle $\theta_5$ are in a range of about $-\pi/2$ to about $\pi/2$. As used herein, angles are expressed in radians where $\pi$ is equal to 180°.

Figure 4:
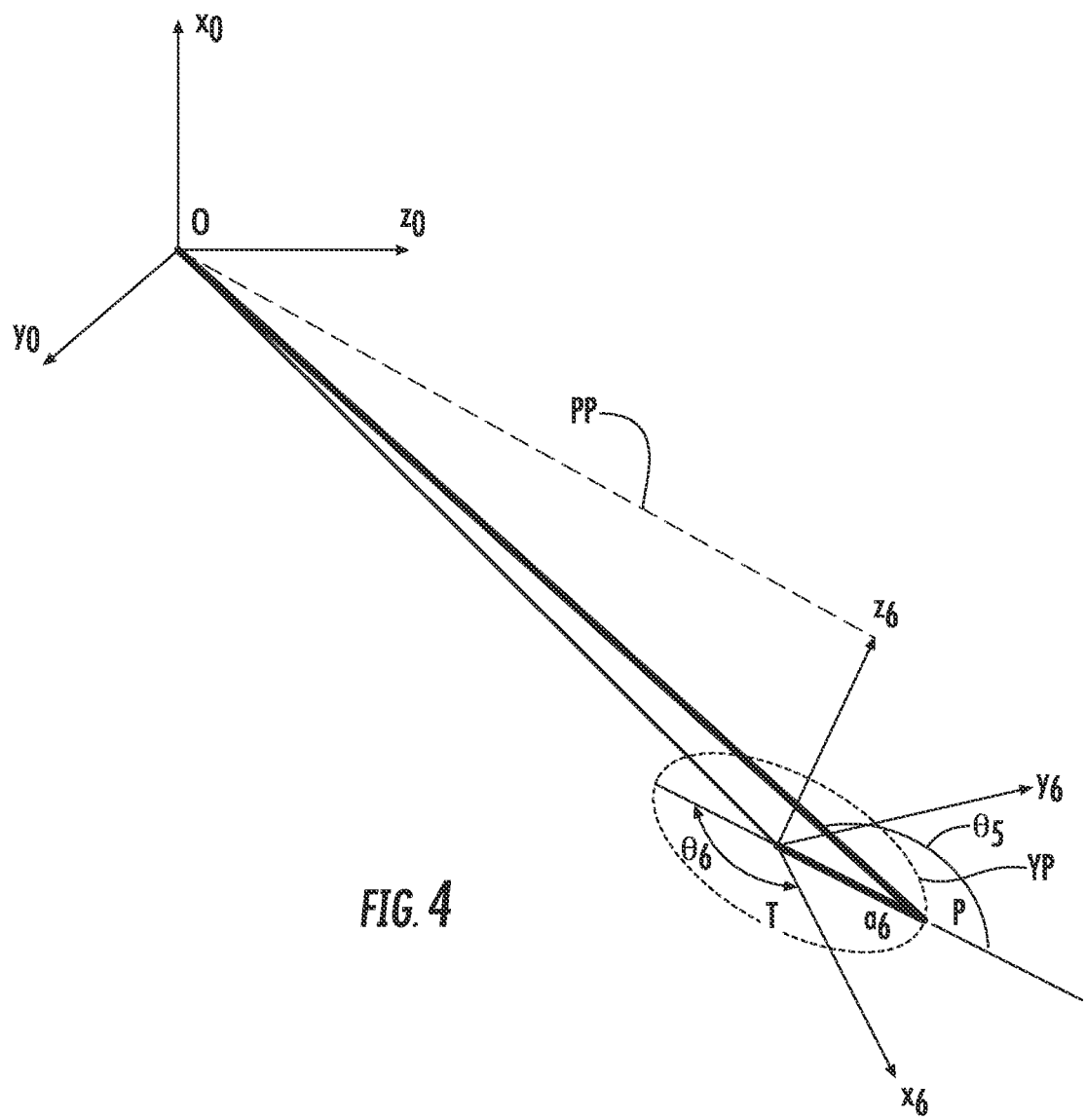
FIG. 4 is a model of the arm and tool of FIG. 2 in a second case.

In the second case modeled in FIG. 4, the pitch plane "PP" is uniquely defined by the trocar point "O" and the $\hat{z}_6$ axis and intersects the yaw plane "YP" at the pitch point "P" on a distal side (i.e., away to the trocar point "O") of the yaw point "T". Thus, in the second case, the joint angle $\theta_6$ and the joint angle $\theta_5$ are outside of a range of about $-\pi/2$ to about $\pi/2$.

Figure 5:
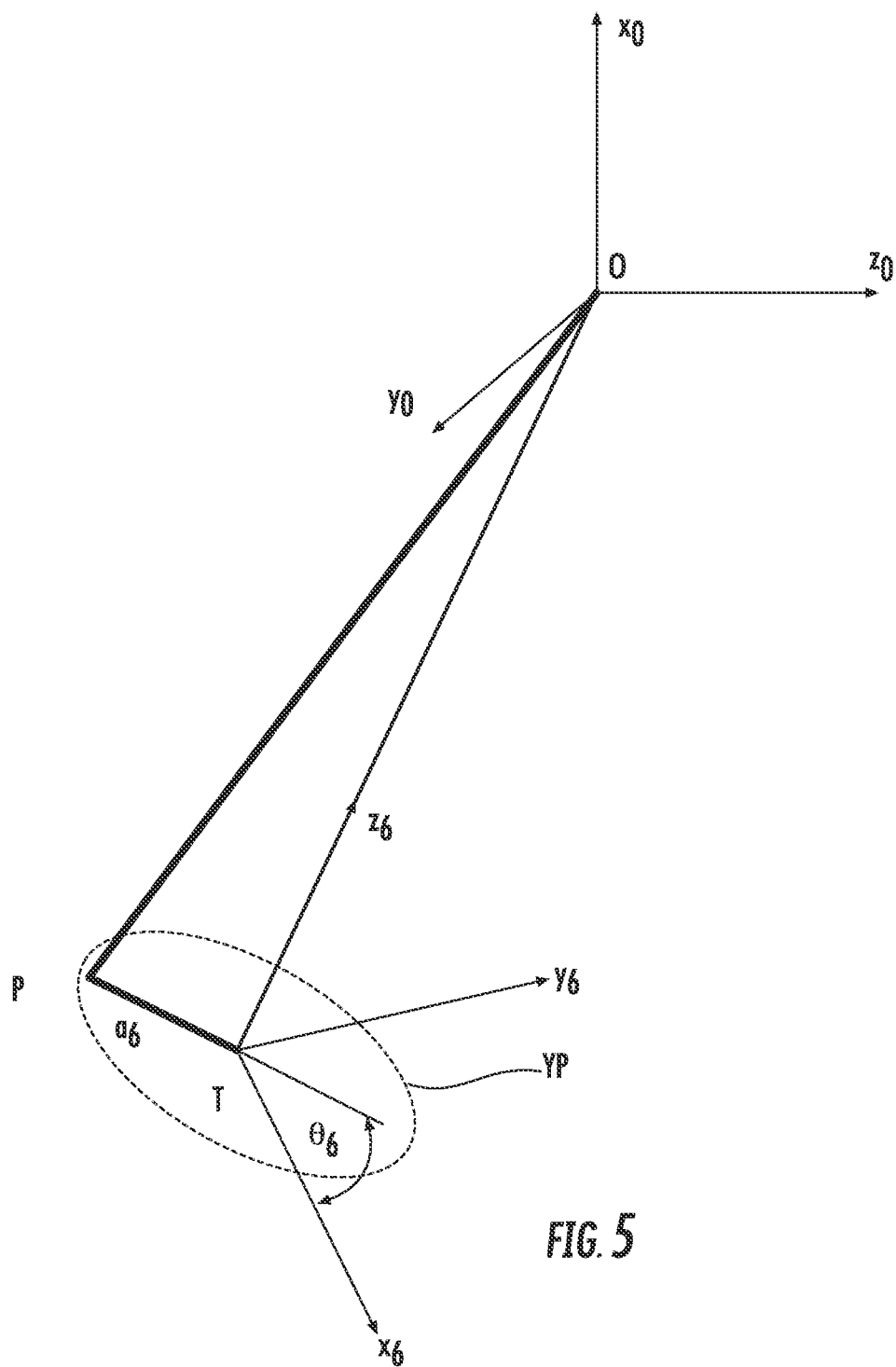
FIG. 5 is a model of the arm and tool of FIG. 2 in a third case.

In the third case modeled in FIG. 5, the $\hat{z}_6$ axis is directed towards the trocar point "O" such that the trocar point "O" and the $\hat{z}_6$ axis fail to uniquely define the pitch plane "PP". In the third case a singularity exists which makes it difficult to determine a range of the joint angle $\theta_6$ and the joint angle $\theta_5$. The third case can be modeled as described in greater detail below.

Referring back to the first case shown in FIG. 3, the determination of the joint angle $\theta_6$, the joint angle $\theta_5$, and the distance $d_4$ is detailed in accordance with the present disclosure. First, assuming that the desired pose of the "TCP" Frame is defined by the position $$\begin{bmatrix} u \\ v \\ w \end{bmatrix}$$

and the rotation $_6^0R$ which are both defined in the Base Frame, the homogenous transform of the "TCP" Frame in the Base Frame can be expressed as:

$$_6^0T = \begin{bmatrix} _6^0R & \begin{bmatrix} u \\ v \\ w \end{bmatrix} \\ 0 & 1 \end{bmatrix} \tag{3}$$

To determine the joint angles, the Base Frame is expressed in the TCP Frame as:

$$_6^0T = \begin{bmatrix} _6^0R & \begin{bmatrix} u' \\ v' \\ w' \end{bmatrix} \\ 0 & 1 \end{bmatrix} \tag{4}$$

Based on the property that $_0^6T=[_6^0T]^{-1}$, $_0^6R=[_6^0R]^{-1}=_6^0R^T$ it can be determined that:

$$\begin{bmatrix} u' \\ v' \\ w' \end{bmatrix} = -_6^0R^T \begin{bmatrix} u \\ v \\ w \end{bmatrix} \tag{5}$$

Figure 6:
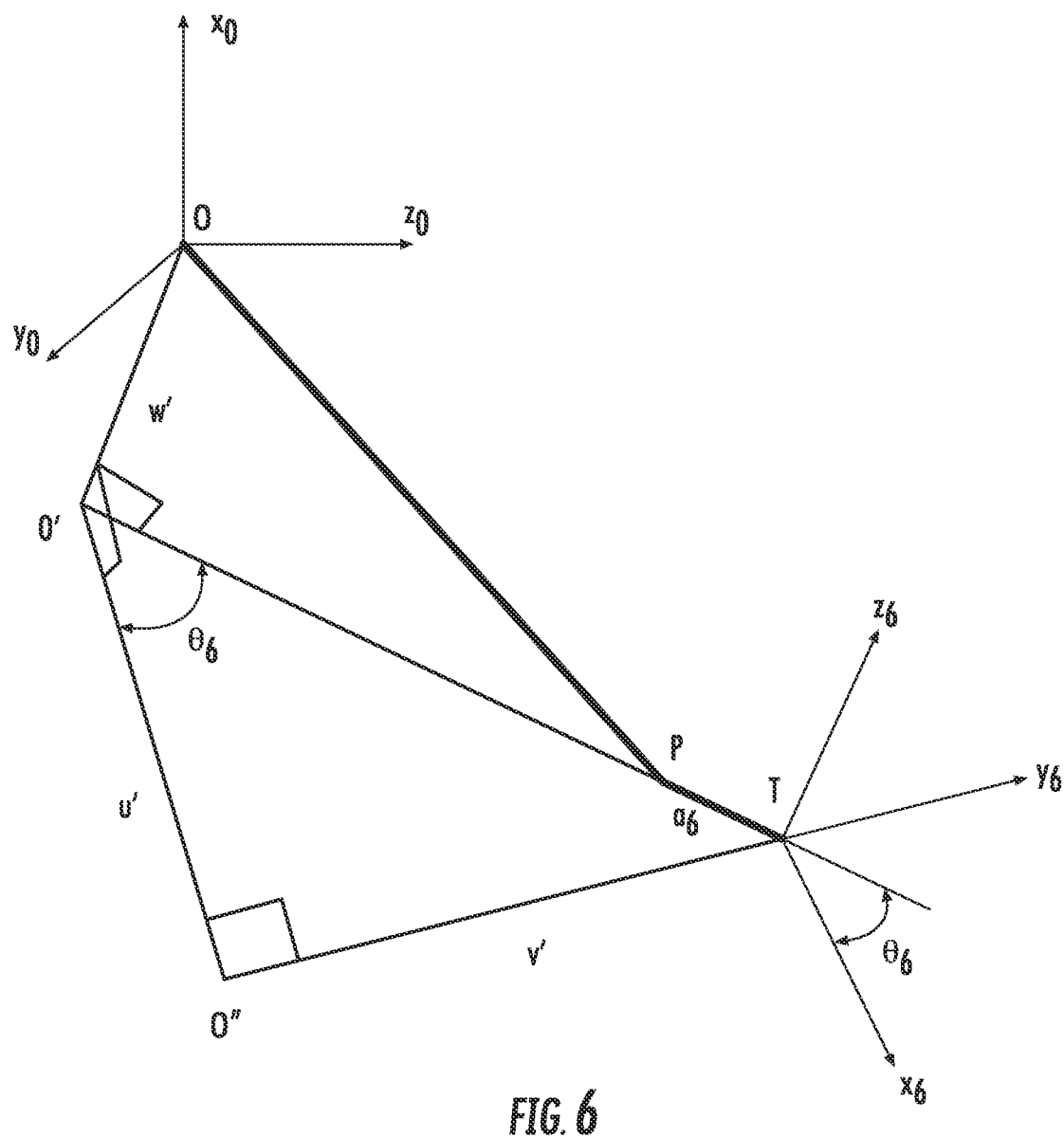
FIG. 6 is the model of FIG. 3 illustrating a calculation of a joint angle $\theta_6$.

Referring now to FIG. 6, the coordinate of the trocar point "O" in the "TCP" Frame is $$\begin{bmatrix} u' \\ v' \\ w' \end{bmatrix}.$$

The projection of the trocar point "O" in the $\hat{x}_6$, $\hat{y}_6$ plane is point "O'" and the projection of point "O" on the $\hat{y}_6$ axis is "O''".

Applying the right hand rule, the relative sign and quarter locations are as follows:

$$\begin{cases} \pi/2 < \theta_6 < \pi, & \text{when } u' > 0, v' > 0; \\ 0 < \theta_6 < \pi/2, & \text{when } u' < 0, v' > 0; \\ -\pi/2 < \theta_6 < 0, & \text{when } u' < 0, v' < 0; \\ -\pi < \theta_6 < -\pi/2, & \text{when } u' > 0, v' < 0 \end{cases} \tag{6}$$

Taking into account the relative sign and quarter location, as detailed above, in Equation 6:

$$\theta_6 = a\tan 2(v', -u') \tag{7}$$

Figure 7:
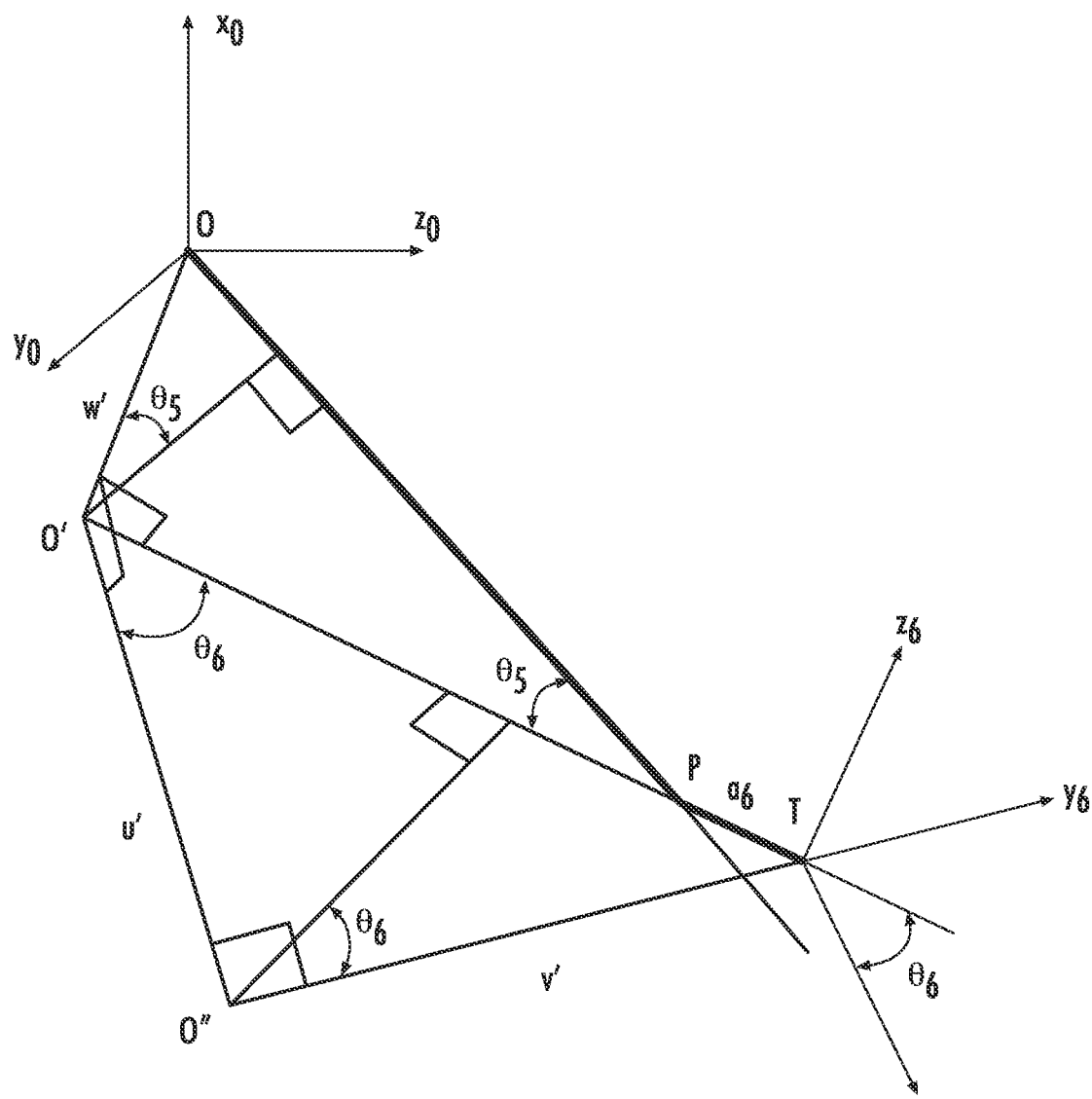
FIG. 7 is the model of FIG. 6 illustrating a calculation of a joint angle $\theta_5$.

With reference to FIG. 7, the distance between the yaw point "T" and point "O'" is given by TO'$=-u'\cos\theta_6+v'\sin\theta_6$ and the distance between the pitch point "P" and point "O'" is given by PO'$=-u'\cos\theta_6+v'\sin\theta_6-a_6$. Thus, the joint angle $\theta_5$ is given by:

$$\theta_5 = a\tan 2(w', -u'\cos\theta_6+v'\sin\theta_6-a_6) \tag{8}$$

In addition, the distance $d_4$ between the trocar point "O" and the pitch point "P" is:

$$d_4 = w'\sin\theta_5+(-u'\cos\theta_6+v'\sin\theta_6-a_6)\cos\theta_5 \tag{9}$$

Now that the joint angle $\theta_6$, the joint angle $\theta_5$, and the distance $d_4$ have been determined, the joint angle $\theta_6$, the joint angle $\theta_5$, and the distance $d_4$ can be used to determine the joint angle $\theta_1$, the joint angle $\theta_2$, and the joint angle $\theta_3$. In light of Equation 2 above, a rotation matrix chain can be expressed as:

$$_6^0R = {_1^0R}\,{_2^1R}\,{_3^2R}\,{_4^3R}\,{_5^4R}\,{_6^5R} \tag{10}$$

Since joint angle $\theta_5$ and joint angle $\theta_6$ are now known, in view of Equation 1, $_6^5R$ can be expressed as:

$$_6^5R = \begin{bmatrix} c\theta_6 & -s\theta_6 & 0 \\ 0 & 0 & 1 \\ -s\theta_6 & -c\theta_6 & 0 \end{bmatrix} \tag{11}$$

In addition, $_5^4R$ can be expressed as:

$$_5^4R = \begin{bmatrix} s\theta_5 & c\theta_5 & 0 \\ 0 & 0 & 1 \\ c\theta_5 & -s\theta_5 & 0 \end{bmatrix} \tag{12}$$

The transpose of the product of the above two equations is expressible as:

$$\left(_5^4R\,_6^5R\right)^T = \begin{bmatrix} s\theta_5 c\theta_6 & -s\theta_6 & c\theta_5 c\theta_6 \\ -s\theta_5 s\theta_6 & -c\theta_6 & -c\theta_5 s\theta_6 \\ c\theta_5 & 0 & -s\theta_5 \end{bmatrix} \tag{13}$$

Then multiplying Equation 13 from the right side to Equation 10:

$$_6^0R\left(_5^4R\,_6^5R\right)^T = {_6^0R}\left(_5^4R\,_6^5R\right)^{-1} = {_1^0R}\,{_2^1R}\,{_3^2R}\,{_4^3R}\,{_5^4R}\,{_6^5R}$$
$$\left(_5^4R\,_6^5R\right)^{-1} = {_4^0R} \tag{14}$$

Further, by defining $$_4^0R \triangleq \bar{R} = \begin{bmatrix} \bar{R}_{11} & \bar{R}_{12} & \bar{R}_{13} \\ \bar{R}_{21} & \bar{R}_{22} & \bar{R}_{23} \\ \bar{R}_{31} & \bar{R}_{32} & \bar{R}_{33} \end{bmatrix}$$

provides that:

$$\begin{bmatrix} \overline{R}_{11} & \overline{R}_{12} & \overline{R}_{13} \\ \overline{R}_{21} & \overline{R}_{22} & \overline{R}_{23} \\ \overline{R}_{31} & \overline{R}_{32} & \overline{R}_{33} \end{bmatrix} = {}_6^0R \begin{bmatrix} s\theta_5 c\theta_6 & -s\theta_6 & c\theta_5 c\theta_6 \\ -s\theta_5 s\theta_6 & -c\theta_6 & -c\theta_5 s\theta_6 \\ c\theta_5 & 0 & -s\theta_5 \end{bmatrix} \quad (15)$$

Figure 8:
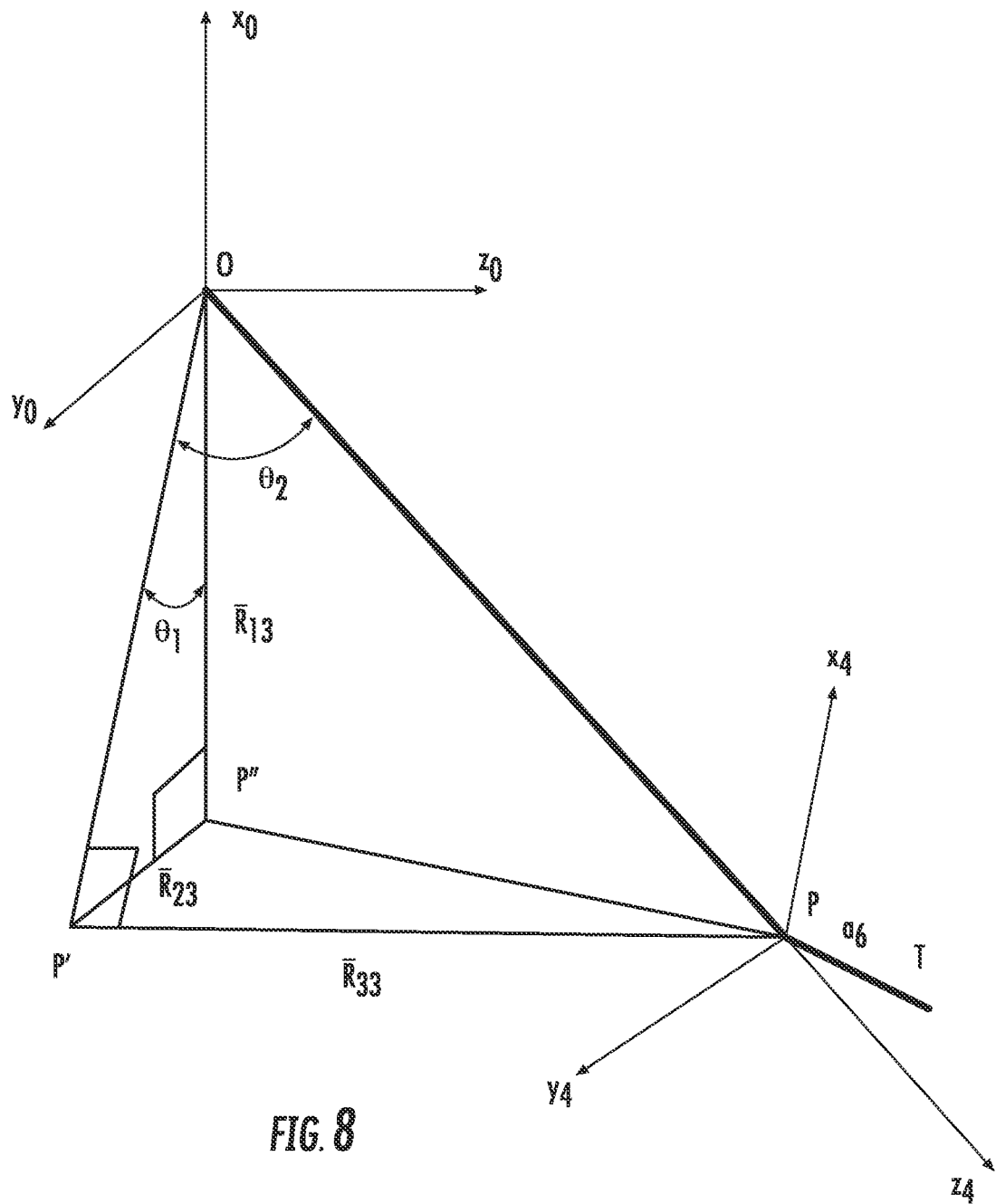
FIG. 8 is the model of FIG. 7 illustrating a calculation of joint angles $\theta_1$ and $\theta_2$.

Referring to FIG. 8, the projection of the pitch point "P" in the $\hat{x}_0$, $\hat{y}_0$ plane is point "P"' and the projection of the point "P"' on the $\hat{x}_0$ axis is "P"'. Thus, P'P''=$-\overline{R}_{23}$·OP and OP''=$-\overline{R}_{13}$·OP. Accordingly, the joint angle $\theta_1$ can be expressed as:

$$\theta_1 = a\tan 2(-\overline{R}_{23}, -\overline{R}_{13}) \quad (16)$$

In addition, joint angle $\theta_2$ can be expressed as:

$$\theta_2 = a\tan 2(\overline{R}_{33}, \sqrt{\overline{R}_{13}^2 + \overline{R}_{23}^2}) \quad (17)$$

It can be observed that when $\theta_2 = \pm \pi/2$, shaft OP of the arm 12 or tool 20 (FIG. 2) is aligned with the rotation axis of joint 1. This is a singularity where joint angle $\theta_1$ and joint angle $\theta_3$ are not uniquely defined. A robot can be designed in such a way that the joint angle θ2 is mechanically constrained to or in a range (e.g., about −70° to about) 70°. In such a range, $\theta_2$ will not reach the singularity. In normal operation, this singularity is checked and rejected by the processing unit 30 (FIG. 1).

Figure 9:
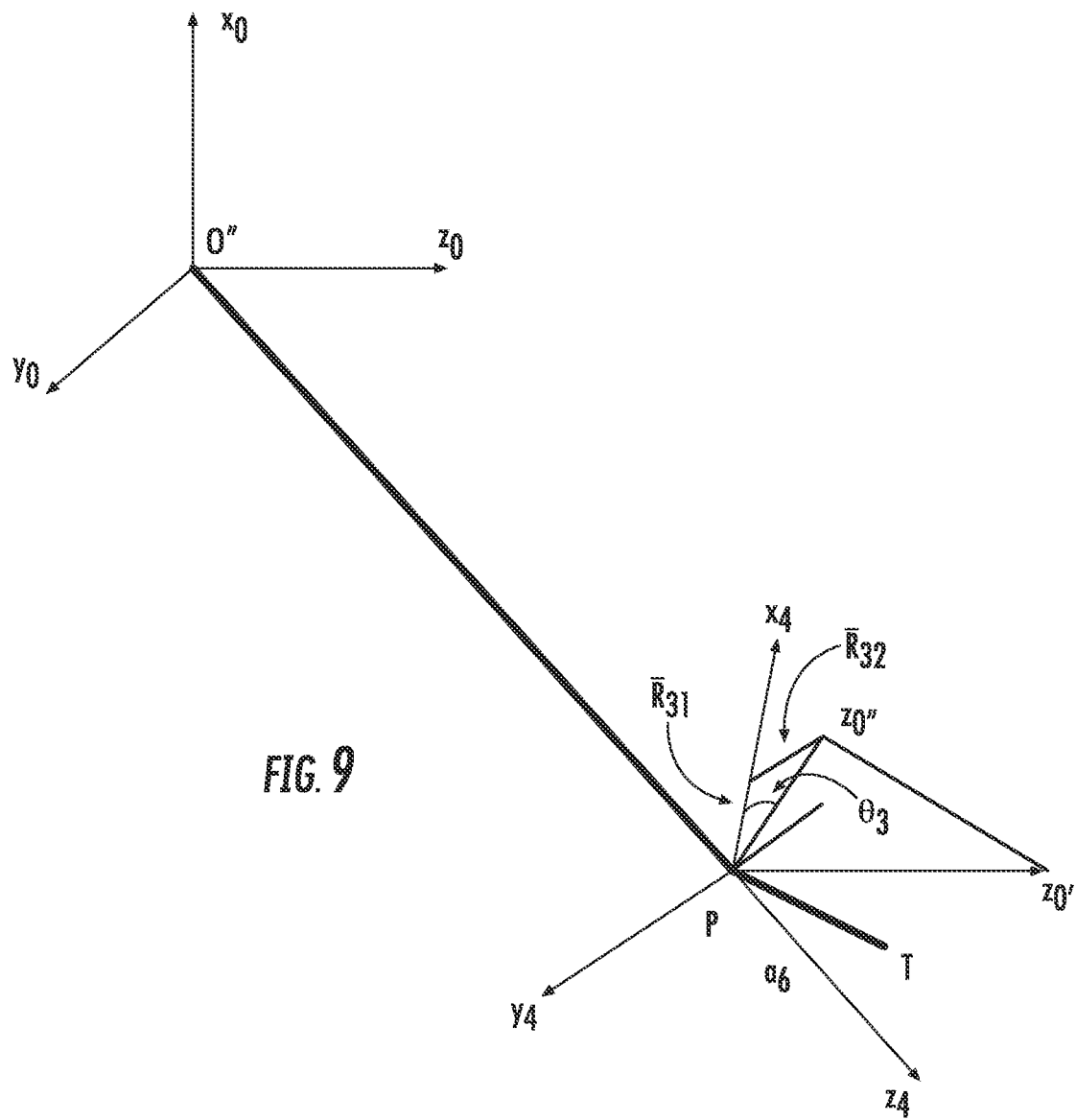
FIG. 9 is the model of FIG. 8 illustrating a calculation of a joint angle $\theta_3$.

With reference to FIG. 9, a $\hat{z}_{0'}$ axis is created at the pitch point "P" that is parallel to the $\hat{z}_0$ axis, the projection point $z_{0'}$ in the plane $\hat{x}_4$, $\hat{y}_4$ is point $z_{0''}$. Thus, the joint angle $\theta_3$ can be expressed as:

$$\theta_3 = a\tan 2(-\overline{R}_{32}, \overline{R}_{31}) \quad (18)$$

Using the previous derivation of the rotation matrix above, if the unit vector of the frame is defined as $\hat{x}$, $\hat{y}$, $\hat{z}$, the equation 15 can be expressed as:

$$\begin{bmatrix} \overline{R}_{11} & \overline{R}_{12} & \overline{R}_{13} \\ \overline{R}_{21} & \overline{R}_{22} & \overline{R}_{23} \\ \overline{R}_{31} & \overline{R}_{32} & \overline{R}_{33} \end{bmatrix} = \begin{bmatrix} \hat{x}_4 \cdot \hat{x}_0 & \hat{y}_4 \cdot \hat{x}_0 & \hat{z}_4 \cdot \hat{x}_0 \\ \hat{x}_4 \cdot \hat{y}_0 & \hat{y}_4 \cdot \hat{y}_0 & \hat{z}_4 \cdot \hat{y}_0 \\ \hat{x}_4 \cdot \hat{z}_0 & \hat{y}_4 \cdot \hat{z}_0 & \hat{z}_4 \cdot \hat{z}_0 \end{bmatrix} \quad (19)$$

With respect to the second case, shown in FIG. 4, the solution for the joint angle $\theta_6$ is labeled $\theta_{6'}$. It will be appreciated that as shown in FIG. 4:

$$\theta_6 - \theta_{6'} = \pi \quad (20)$$

Thus, to determine the joint angles in the second case, the joint angle $\theta_6$ is calculated in a manner similar to the first case detailed above and then Equation 20 is used to determine the joint angle $\theta_{6'}$ for the second case. Once the joint angle $\theta_{6'}$ for the second case is determined, the rest of the joint angles $\theta_1$, $\theta_2$, $\theta_3$, and $\theta_5$ as well as the distance $d_4$ can be determined using the above method.

Now turning to the third case, as shown in FIG. 5, the third case can be detected when $$\begin{cases} u' \cong 0; \\ v' \cong 0 \end{cases} \quad (21)$$

If the singularity of the third case is detected, the previous joint angle $\theta_6$ can be used. Thus, with $\theta_6 = \theta_{6,previous}$, the rest of the joint angles $\theta_1$, $\theta_2$, $\theta_3$, and $\theta_5$ as well as the distance $d_4$ can be determined using the above method.

As detailed above, the inverse kinematics solution provides mathematically precise mapping between an input pose and joint angles of the surgical robot 10. In the inverse kinematics solution, other considerations such as joint limits and joint speed limits are not taken into account. For example, due to mechanical constraints of the design of the surgical robot 10, the joint limits of joint angles $\theta_5$ and $\theta_6$ are usually in the range of about $-\pi/2$ to about $\pi/2$. The mechanical constraints of the surgical robot 10 prevent cases 2 and 3, detailed above, from being physically realizable since one of the joint angles will be greater than $\pi/2$. However, the poses presented in cases 2 and 3 may be commanded by the input device 42 because the input device 42 and the surgical robot 10 have different kinematic constructions and working spaces. For example, case 3 is a singularity where the inverse kinematic solution is not unique. In addition, when the joint angle $\theta_5$ approaches $\pm \pi/2$, a small rotation of the input pose along the axis $x_6$ would cause a dramatic change in joint angle $\theta_3$. Such a dramatic change may violate a joint speed limit and an acceleration limit of the roll joint of the arm 12 represented by joint angle $\theta_3$. It will be appreciated that such sudden motions are undesirable in clinical settings.

To avoid an unrealizable configuration or a singularity condition, the joint angle $\theta_5$ is restricted in a range of about $-5\pi/12$ to about $5\pi/12$ and the joint angle $\theta_6$ is restricted in a range of about $-\pi/2$ to about $\pi/2$. One method of achieving this is in a brutal-force method by clamping the solution provided by the inverse kinematics solution. However, the brutal-force method may cause discontinuity in the inverse kinematics solution which is not desirable in a clinical setting.

Alternatively, as detailed below, a method may be used to correct the input pose after it crosses from a desirable solution space to an undesirable solution space. In the desirable solution space, the joint limits and the joint speed limits are acceptable and in the undesirable solution space at least one of the joint limits or the joint speed limits are exceeded or undesirable. Once the input pose is corrected, the corrected input pose can be solved by using the inverse kinematics solution detailed above having deniable joint angles. Such a method may avoid discontinuities in the joint angles when the boundary between the desirable and undesirable solution spaces is crossed. In addition, such a method can realize the position component of the input pose by only correcting an orientation component of the TCP frame to avoid unintended motion of the TCP frame from being introduced into the inverse kinematic solution.

As described below, a projection method that corrects an orientation component of the TCP frame of a desired input pose while maintaining a position component of the desired input pose is disclosed in accordance with the present disclosure. In the projection method, a boundary plane that separates a desirable and undesirable solution space may be defined by locating the trocar point on a spherical surface. A boundary plane then divides the spherical surface into two sections. If the trocar point is located on one side of the boundary (e.g., the right side), the input pose does not require correction. If no correction is required, the inverse kinematics solutions are desirable and within the joint limits and the joint speed limits. When the trocar point is located on the other side of the boundary (e.g., the left side), the input pose is projected to the boundary plane. If correction is required, the input pose is corrected by rotating the TCP frame to a projection point located on the boundary plane according to rigid body kinematics and expressing the corrected TCP frame in a rotated base frame for the inverse kinematics solution. After the correction of the TCP frame, the inverse kinematics solution for the corrected TCP frame will be desirable and within the joint limits and the joint speed limits.

With reference to FIGS. 10-15, a method of correcting an input pose for the arm 12 and the tool 20 (FIG. 2) in the event of the desired input pose being in an undesirable solution space (i.e., case 2, case 3, or a singularity) will be described in detail. Knowing that the joint angle $\theta_6$ is physically limited to about $-\pi/2$ to about $\pi/2$ and that the joint angle $\theta_5$ is physically limited to about $-\pi/2$ to about $\pi/2$, the projection of the trocar point "O" in the plane $\hat{x}_6$, $\hat{y}_6$ lies in region "S" of FIG. 10.

When the projection point "O'" of the trocar point "O" is close to a circle about the yaw point "T" with a radius equal to the length $a_6$ of the yoke "PT", the joint angle $\theta_5$ will approach $\pm\pi/2$. Thus, any small orientation change of the $\hat{z}_6$ axis will cause a large change in the joint angle $\theta_6$ and the joint angle $\theta_2$.

Figure 10:
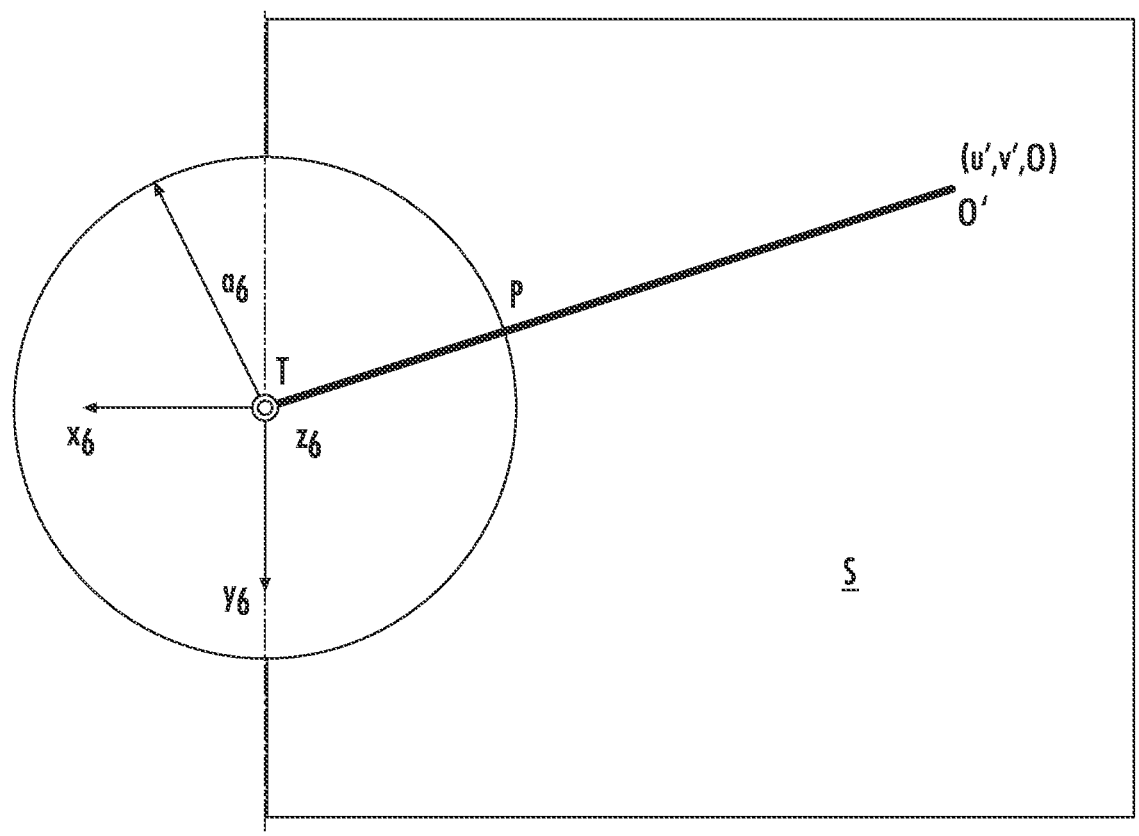
FIG. 10 is a plan view of the $\hat{x}_6, \hat{y}_6$ plane of the model of FIG. 3.

Continuing to refer to FIG. 10, it will be appreciated that the projection point "O'" cannot lie outside of the region "S" due to the physical limits of joint angle $\theta_6$ and/or joint angle $\theta_5$.

Figure 12:
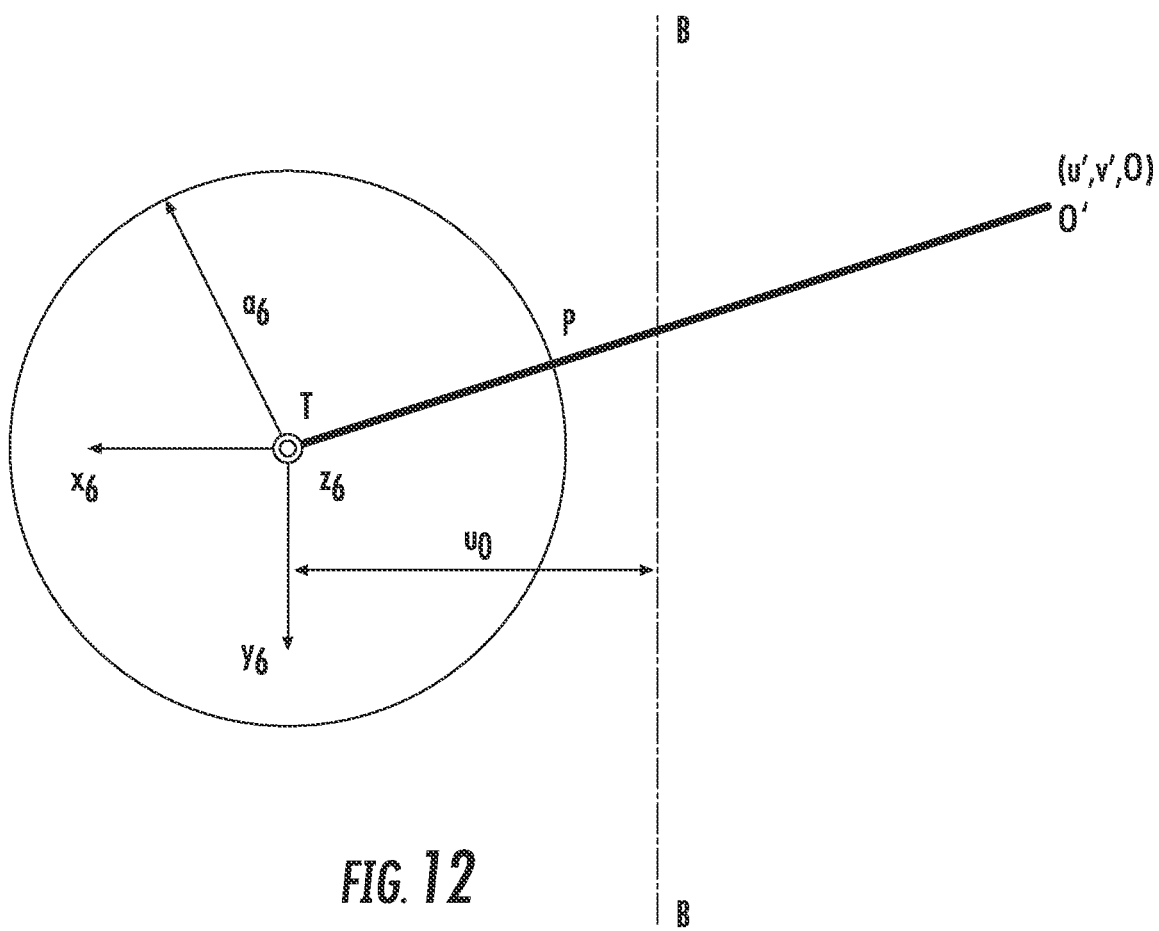
FIG. 12 is the plan view of FIG. 10 including a boundary line B.

Referring to FIG. 12, during operation of the arm 12 and the tool 20, it is desirable that the projection point "O'" is positioned beyond, to the right as shown, of a dotted boundary line "B" with a dimension $u_o$ from the $\hat{y}_6$ axis which is greater than the length $a_6$ of the yoke "PT" which requires that:

$$u' < u_0 \quad (22)$$

The coordinate $u_0$ is chosen to meet the physical limits of joint angle $\theta_5$ and joint angle $\theta_6$ to avoid a singular condition. As described in detail below, the projection point "O'" may be positioned on either side or on the boundary line "B".

Figure 11:
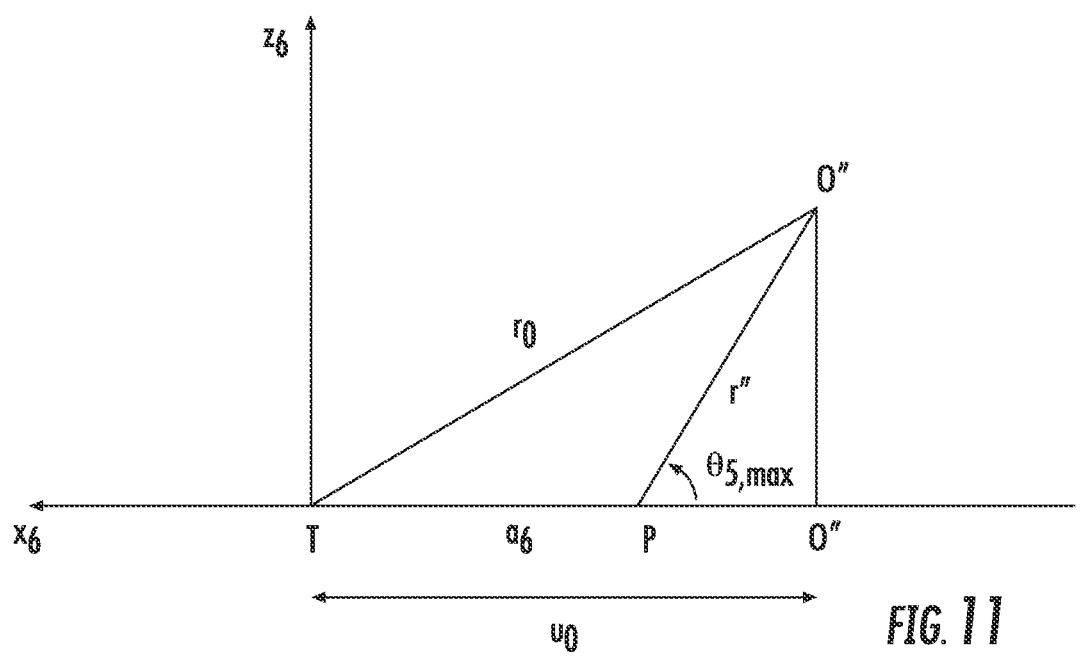
FIG. 11 is a model illustrating determination of $u_0$.

With particular reference to FIG. 11, a distance r" is defined between the projection point "O'" and pitch point "P", such that $$(r''\cos\theta_{5,max}+a_6)^2+(r''\sin\theta_{5,max})^2=r_0^2 \quad (23)$$

From Equation 23, r" can be calculated, and coordinate $u_0$ can be expressed as $$u_0=-(a_6+r''\cos\theta_{5,max}) \quad (24)$$

where $\theta_5$, max is a desirable limit (i.e., mechanical constraint) on joint angle $\theta_5$ (e.g., 75° or $5\pi/12$).

If the projection point "O'" lies on the left side of the boundary line "B", the projection point "O'" is systematically projected to the boundary line "B". In this manner, the yaw point "T" is rotated according to the projection rule, as detailed below, such that after the rotation of the yaw point "T", a new pose of the "TCP" Frame is realized.

Figure 13:
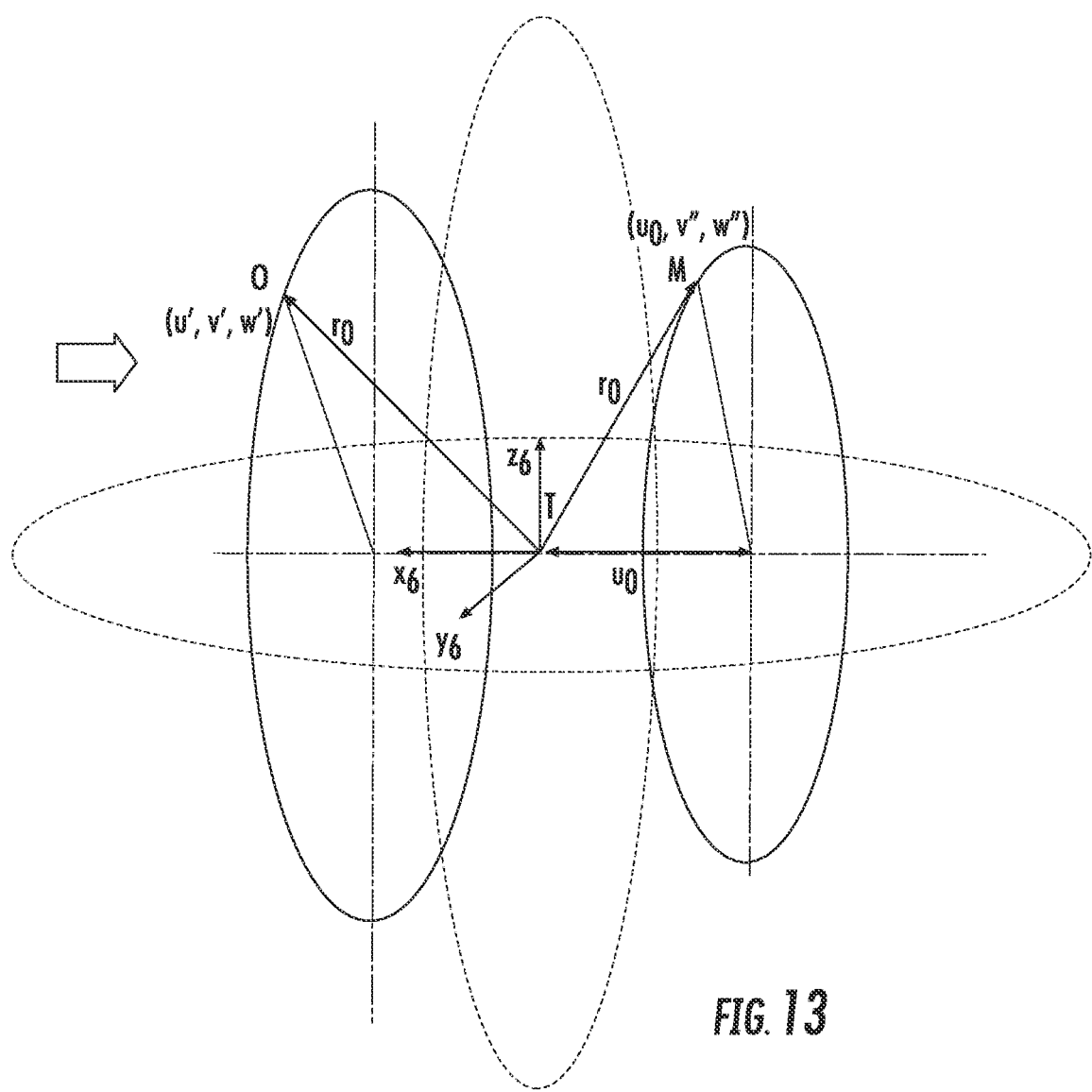
FIG. 13 is a model illustrating a projection method of calculating a rotation of a trocar point O to a rotated trocar point M.
Figure 14:
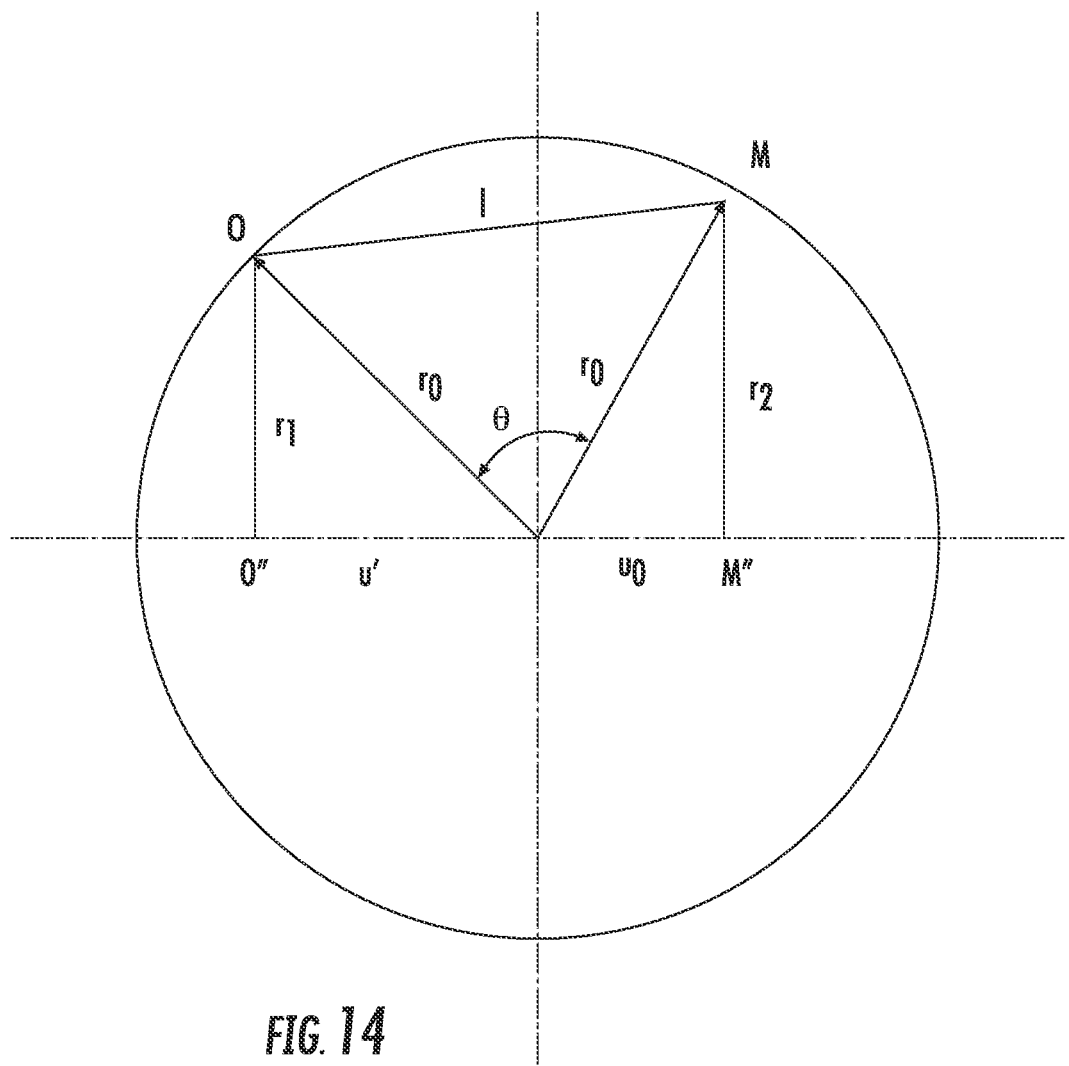
FIG. 14 is a calculation of a rotation angle $\phi$ from the trocar point O to the rotated trocar point M of FIG. 13.

Referring to FIG. 13, the trocar point "O" and the yaw point "T" are connected such that a distance between the yaw point "T" and the trocar point "O" is distance $r_0$. The distance $r_0$ is equal to $\sqrt{u'^2+v'^2+w'^2}$. With the distance $r_0$ held constant, the vector $\vec{TO}$ is rotated in the "TCP" Frame around the yaw point "T" such that the trocar point "O" will travel on a sphere centered at the yaw point "T". When the projection point "O'" lies on the left side of the boundary line "B" as illustrated in FIG. 11, the yaw point "T" will rotate until the trocar point "O" is rotated to the point "M" such that the projection point "O'" lies on the boundary line "B".

During this rotation, the orientation of the vector $\vec{TO}$ in the $\hat{y}_6$, $\hat{z}_6$ plane remains constant. In accordance with the projection rule $$\begin{cases} u''=u_0 \\ v''=kv' \\ w''=kw' \end{cases} \quad (25)$$

Where the linear constant k is given by:

$$k=\sqrt{\frac{r_0^2-u_0^2}{v'^2+w'^2}} \quad (26)$$

Referring to FIG. 13, the rotation angle "ϕ" of the yaw point "T" can be determined as:

$$\phi=2a\sin(l/2r_0) \quad (27)$$

where $l=\sqrt{(u'-u_0)^2+(\sqrt{r_0^2-u'^2}-\sqrt{r_0^2-u_0^2})^2}$.

Figure 15:
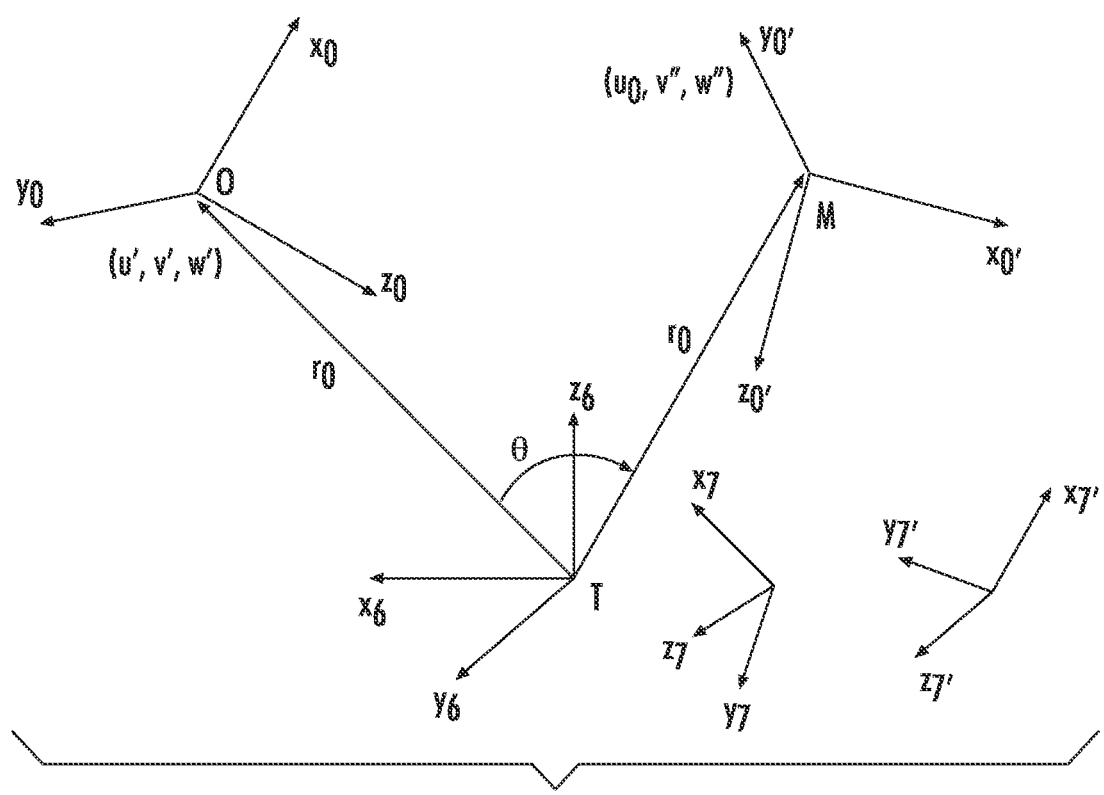
FIG. 15 is a calculation of an orientation matrix for the rotation of the Base Frame $\hat{x}_0, \hat{y}_0, \hat{z}_0$.

Referring now to FIG. 15, new frames $x_7$, $y_7$, $z_7$ (Frame 7) and $x_{7'}$, $y_{7'}$, and $z_{7'}$ (Frame 7') are defined. Both Frames 7 and 7' originate at the yaw point "T". For Frame 7, the $\hat{x}_7$ axis is aligned with the vector $\vec{TO}$ and the $\hat{z}_7$ axis is along the direction of $\vec{TM} \times \vec{TO}$. For Frame 7', the $\hat{x}_{7'}$ axis is aligned with the vector $\vec{TM}$ and the $\hat{z}_{7'}$ axis is along the direction of $\vec{TM} \times \vec{TO}$. After the rotation, the Base Frame becomes frame $x_{0'}$, $y_{0'}$, and $z_{0'}$ (Rotated Base Frame). Thus, when $\phi \leq \pi/2$, $\vec{Tz_7}=\vec{TM}\times\vec{TO}/|\vec{TM}\times\vec{TO}|$, and when $\phi>\pi/2$, $\vec{Tz_7}\times-\vec{TM}\times\vec{TO}/|\vec{TM}\times\vec{TO}|$, the Base Frame expressed from Frame 6 through Frame 7 is:

$$_0^6T=_7^6T_0^7T \quad (28)$$

and the Rotated Base Frame expressed from Frame 6 through Frame 7' is:

$$_{0'}^6T=_{7'}^6T_{0'}^{7'}T \quad (29)$$

During rotation, the Base Frame in Frame 7 is equal to the Rotated Base Frame in Frame 7' such that:

$$_0^7T=_{0'}^{7'}T \quad (30)$$

Thus, the Rotated Base Frame in Frame 6 can be calculated as:

$$_{0'}^6T=_{7'}^6T[_7^6T]^{-1}{_0^6T} \quad (31)$$

From Equation 31 we have:

$$_7^6T=\begin{bmatrix} \hat{x}_{7'} & \hat{y}_{7'} & \hat{z}_{7'} & \begin{bmatrix} u_0 \\ v'' \\ w'' \end{bmatrix} \\ 0 & & & 1 \end{bmatrix} \quad (32)$$

and $$_7^6T=\begin{bmatrix} \hat{x}_7 & \hat{y}_7 & \hat{z}_7 & \begin{bmatrix} u' \\ v' \\ w' \end{bmatrix} \\ 0 & & & 1 \end{bmatrix} \quad (33)$$

During the above posing, it is assumed, for simplicity, that the trocar point "O" and the Base Frame are rotated and that the yaw point "T" and the "TCP" Frame are kept constant. In fact, during the above movement, the trocar point "O", the yaw point "T", and the Base Frame are kept constant and only the "TCP" Frame is rotated. Due to the fact that the rotation is relative, if the "TCP" Frame is rotated instead of the Base Frame, then the rotated "TCP" Frame can be expressed in the Base Frame as:

$$\,_6^0T = \begin{bmatrix} \,_{0'}^{6}R^T & \begin{bmatrix} u \\ v \\ w \end{bmatrix} \\ 0 & 1 \end{bmatrix} \quad (34)$$

where $\,_{0'}^{6}R$ is from the homogenous transform $\,_{0'}^{6}T$ in Equation 31.

Figure 16:
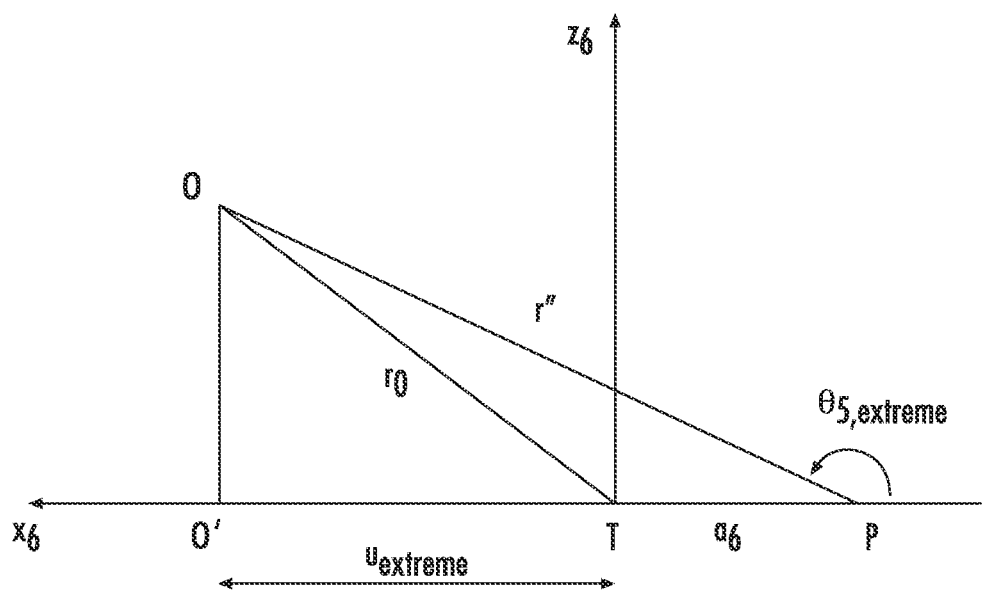
FIG. 16 is a model illustrating detection of an extreme condition.

Referring to FIG. 16, in some extreme conditions, when $u' > u_{extreme}$, another singularity condition is approached. This singularity condition is unlikely due to the range of motion of anatomical limits of the hands of a clinician that are engaged with the input device 43 (FIG. 1). However, when $\theta_5 > \theta_{5,extreme}$ (e.g., 150°), $\hat{x}_6$ is pointing back to the trocar point "O" and the motion of $\hat{x}_6$ will be significantly amplified. The motion from the inverse kinematic solution may become less stable. Accordingly, the algorithm may provide feedback to a clinician informing or warning the clinician that the singularity condition is being approached. In addition, if necessary, the robotic system 10 may decouple or stop the mapping between the input device 43 and the arm 12 of the surgical robot 10. Similar to the determination of $u_0$ in Equations 23 and 24, the distance between trocar point "O" and pitch point "P" can be expressed as:

$$(r'' \cos(\pi - \theta_{5,extreme}) - a_6)^2 + (r'' \sin(\pi - \theta_{5,extreme}))^2 = r_0^2 \quad (35)$$

Solving for r" from the above equation 35 provides:

$$u_{extreme} = r'' \cos(\pi - \theta_{5,extreme}) - a_6 \quad (36)$$

In light of the above, the steps of the complete inverse kinematics algorithm for the arm 12 and the tool 20 (FIG. 2) are:

1) For each given input pose $\,_6^0T$, calculate the trocar point "O" position in the TCP frame using Equation 5;
2) Use Equation 22 to check if the input pose needs correction, if correction is needed got to step 3, otherwise, skip to step 5;
3) Check if $u' > u_{extreme}$ with Equation 35, if true provide feedback, else got to Step 4;
4) Use Equations 23 to 31 to calculate a corrected pose $\,_6^0T$, and replace the original pose with the corrected pose;
5) Use Equations 6 to 18 to calculate the joint angles $\theta_1$, $\theta_2$, $\theta_3$, $\theta_5$, and $\theta_6$ as well as the distance $d_4$.

In the inverse kinematics algorithm above, checking if the input pose needs correction is accomplished by choosing $u_0$ in Equation 22 as a function of the yaw point "T" and a maximum joint angle $\theta_{5,\,max}$. For example, the maximum joint angle $\theta_{5,\,max}$ may be selected as $5\pi/12$ (i.e., 75°).

As detailed above, the tool 20 (FIG. 2) has two DOF in addition to a grasping function. It is contemplated that other tools may be used with this inverse kinematic model by manipulating constraints of the joint angles as detailed below.

When the tool 20 is a straight instrument, the joint angle $\theta_5$ and the joint angle $\theta_6$ are about zero such that the straight instrument is treated as a wristed instrument. Accordingly, Equation 23 can be modified as follows:

$$\begin{cases} u'' = k' u' \\ v'' = 0 \\ w'' = k' w' \end{cases} \quad (37)$$

When the tool 20 is a stapler instrument, a jaw (not shown) of the stapler instrument is typically pivotal in one DOF such that the joint angle $\theta_6$ is substantially zero. Thus, Equation 23 can be modified as follows:

$$\begin{cases} u'' = k' u' \\ v'' = 0 \\ w'' = k' w' \end{cases} \quad (38)$$

where $k' = \dfrac{r_0}{\sqrt{u'^2 + w'^2}}$, and the rest of the algorithm detailed above continues to operate properly with a stapler instrument as the tool 20.

When the tool 20 is another type of instrument with a single DOF the joint angle $\theta_5$ may be substantially zero. Similar to the stapler instrument above, Equation 23 can be modified such that:

$$\begin{cases} u'' = k' u' \\ v'' = k' v' \\ w'' = 0 \end{cases} \quad (39)$$

where $k'' = \dfrac{r_0}{\sqrt{u'^2 + v'^2}}$, and the rest of the algorithm detailed above continues to operate properly with such an instrument.

It will be appreciated that Equations 37-39 are applied after the correction Equations 25-34 have been applied. Thus, two rounds of corrections are required.

Figure 17:
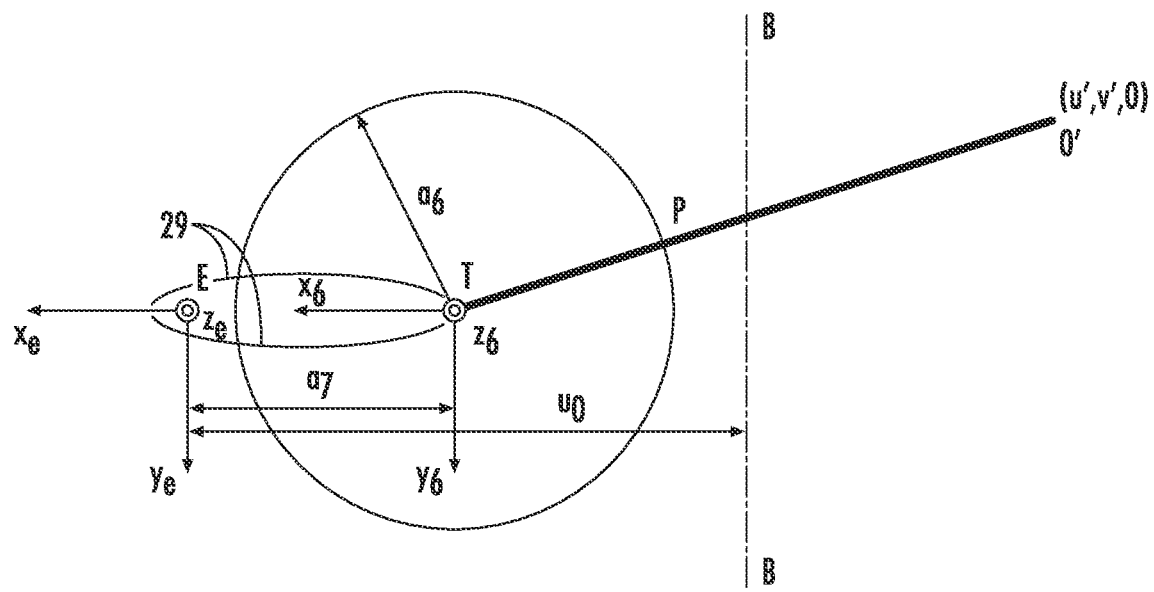
FIG. 17 is a model of a long jawed instrument with the arm of the robotic system of FIG. 1 in accordance with the present disclosure.

When tool 20 is an instrument with long jaws 29 (e.g., a bowel grasper), an additional frame may be needed. As shown in FIG. 17, a frame $x_e$, $y_e$, $z_e$ (End Effector Frame) is defined orientated similar to Frame 6 and offset a distance $a_7$ from Frame 6. As shown, the End Effector Frame is defined adjacent a tip of the long jaws 29 along a centerline of the long jaws 29. It is contemplated that the End Effector Frame may be on the centerline of the long jaws 29, in a middle of the long jaws 29, or any point along or between the long jaws 29.

Figure 18:
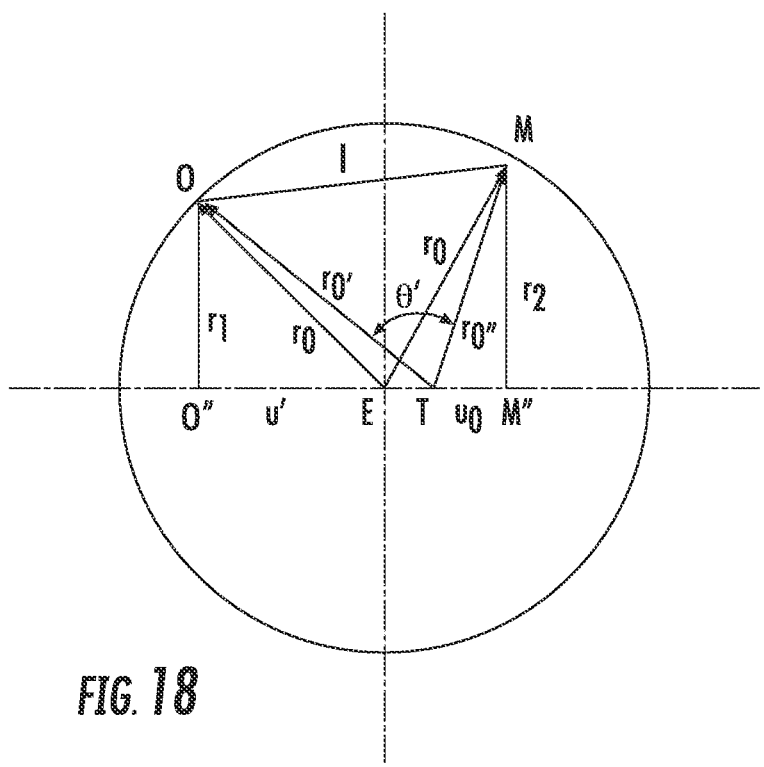
FIG. 18 is a calculation of a rotation angle $\phi$ in a Frame 6 of the trocar point O to the rotated trocar point M of FIG. 17.
Figure 19:
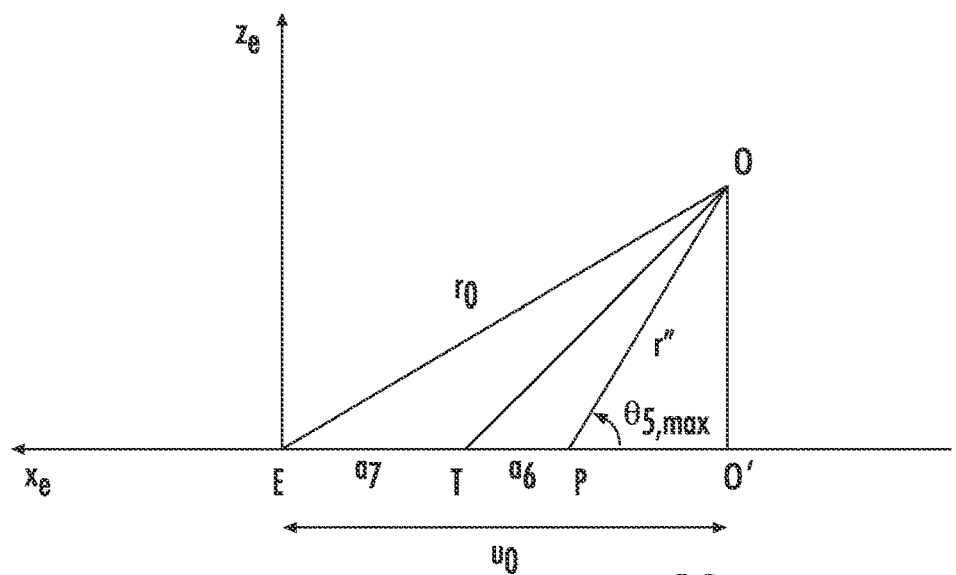
FIG. 19 is a model illustrating determination of $u_0$ for the long jawed instrument of FIG. 17.
Figure 20:
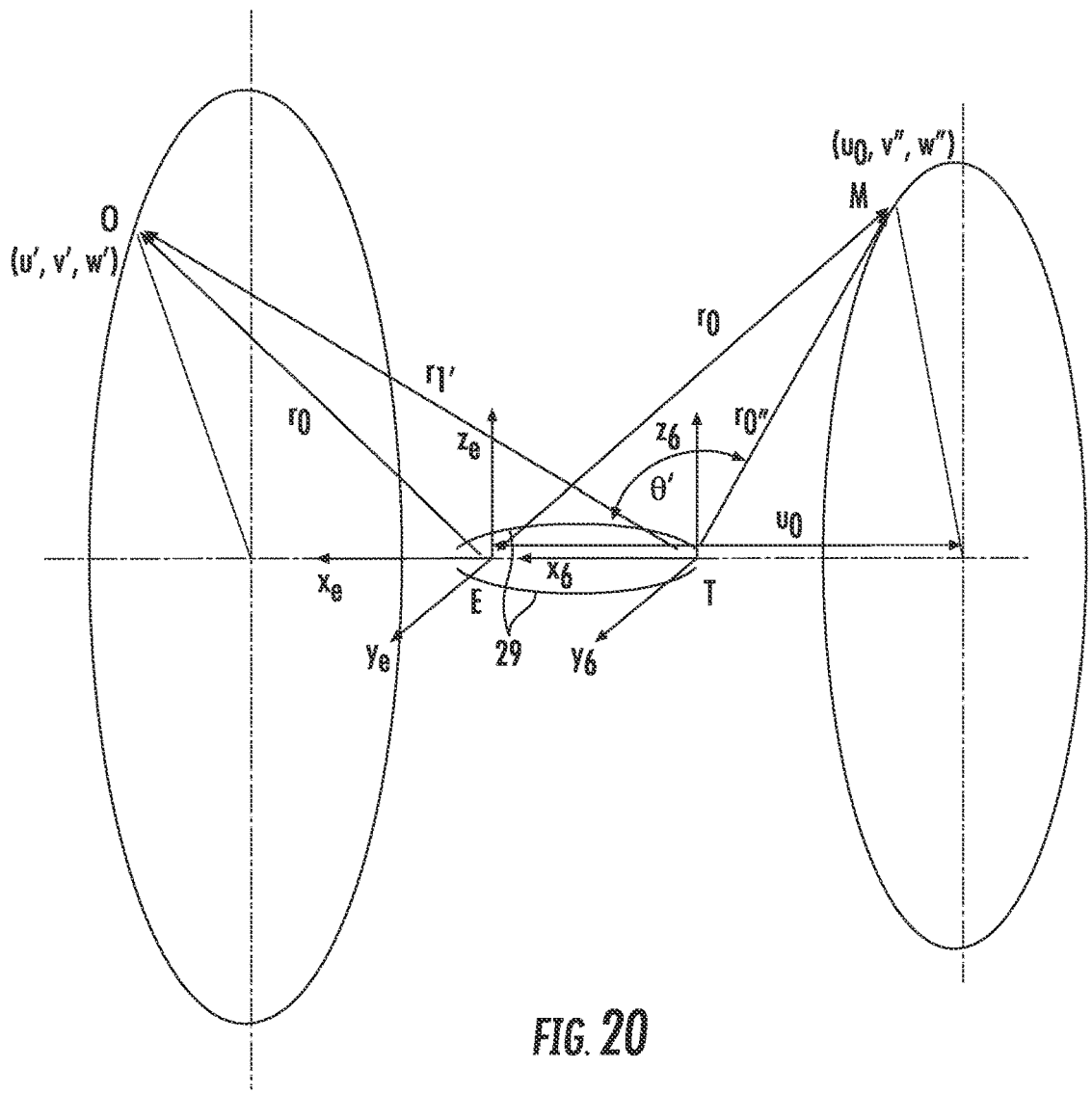
FIG. 20 is a projection of an End Effector Frame of FIG. 17 to the rotated trocar point M

Referring to FIGS. 18-20, the determination of $u_0$ needs to contemplate the distance $a_7$. With particular reference to FIG. 19, similar to the derivation of Equation 23

$$(r'' \cos \theta_{5,max} + a_6 + a_7)^2 + (r'' \sin \theta_{5,max})^2 = r_0^2 \quad (40)$$

Solving for r" in Equation 40, coordinate $u_0$ can be expressed as:

$$u_0 = -(a_6 + a_7 + r'' \cos \theta_{5,max}) \quad (41)$$

Following the projection method as detailed above, Equation 3 becomes:

$$\,_6^0T = \begin{bmatrix} \,_6^0R & \begin{bmatrix} u \\ v \\ w \end{bmatrix} \\ 0 & 1 \end{bmatrix} \quad (42)$$

Expressing the Base Frame in the End Effector Frame provides:

$$\,_6^0T = \begin{bmatrix} \,_6^0R & \begin{bmatrix} u' \\ v' \\ w' \end{bmatrix} \\ 0 & 1 \end{bmatrix} \quad (43)$$

and the position of the trocar point "O" in the End Effector Frame is:

$$\begin{bmatrix} u' \\ v' \\ w' \end{bmatrix} = -{}_6^0R^T \begin{bmatrix} u \\ v \\ w \end{bmatrix} \quad (44)$$

Referring to FIG. 18, u' is constrained according to Equation 22. If $u'>u_0$, where $u_0$ can be dynamically constrained by using Equation 40, the trocar point "O" is projected to rotated trocar point "M" as shown in FIG. 20. The coordinates of the rotated trocar point "M" is calculated according to Equation 25.

As shown in FIG. 18, the distance between trocar point "O" and rotated trocar point "M" is:

$$l = \sqrt{(u'-u_0)^2 + (\sqrt{r_0^2 - u'^2} - \sqrt{r_0^2 - u_0^2})^2} \quad (45)$$

and the distance between the trocar point "O" and the yaw point "T" is:

$$r'_0 = \sqrt{r_0^2 - u'^2 + (u'+a_7)^2} \quad (46)$$

and the distance between the yaw point "T" and the rotated trocar point "M" is:

$$r''_0 = \sqrt{r_0^2 - u_0^2 + (-u_0 - a_7)^2} \quad (47)$$

The rotation angle $\phi'$ can be expressed as:

$$\phi' = a\cos\left(\frac{l^2 - r'^2_0 - r''^2_0}{2r'_0 r''_0}\right) \quad (48)$$

Figure 21:
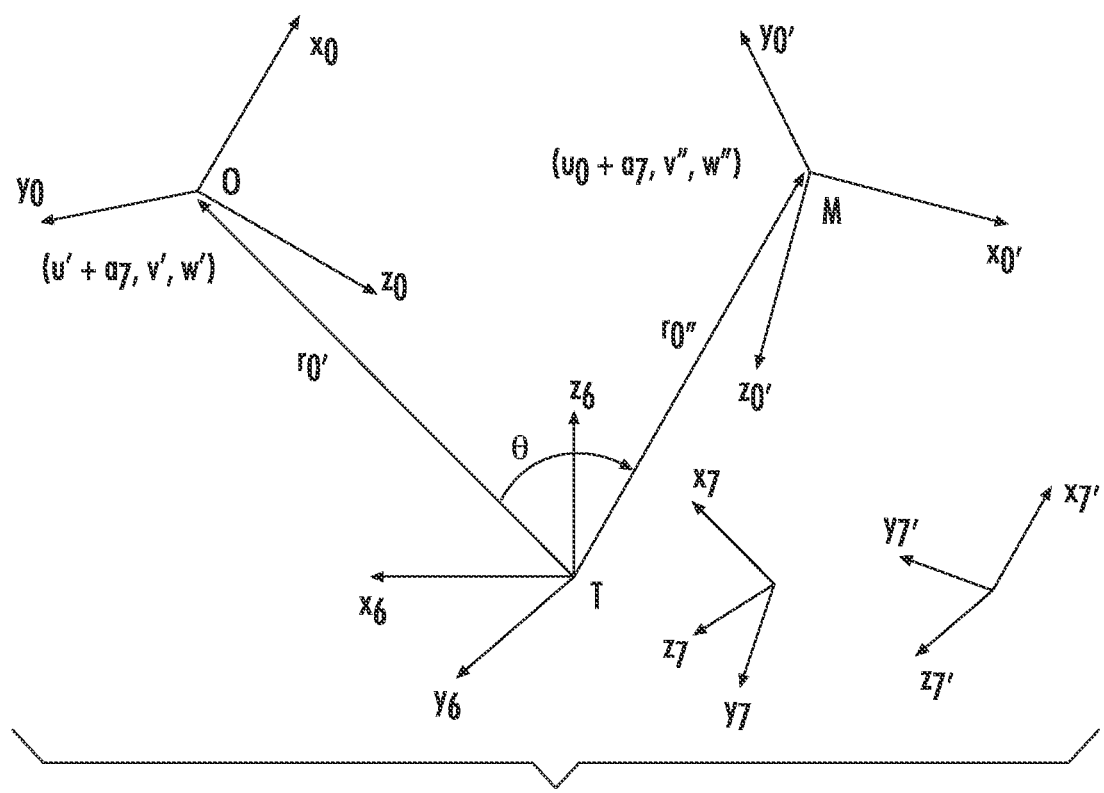
FIG. 21 is a calculation of an orientation matrix for the rotation of the Frame 6.

Referring to FIG. 21, following a similar derivation to that of Equations 25-34, the rotation angle is $\phi'$ instead of $\phi$. It will be appreciated that Equation 31 remains accurate; however, Equation 32 changes to the following:

$$^6_7T = \begin{bmatrix} \hat{x}_{7'} & \hat{y}_{7'} & \hat{z}_{7'} & \begin{bmatrix} 0 \\ 0 \\ 0 \end{bmatrix} \\ 0 & & & 1 \end{bmatrix} \quad (49)$$

and Equation 33 becomes the following:

$$^6_7T = \begin{bmatrix} \hat{x}_7 & \hat{y}_7 & \hat{z}_7 & \begin{bmatrix} 0 \\ 0 \\ 0 \end{bmatrix} \\ 0 & & & 1 \end{bmatrix} \quad (50)$$

and further:

$$^0_eT = {}^0_6T\,{}^6_eT \quad (51)$$

and $^0_6T$ can be expressed as:

$$^0_6T = {}^0_eT[{}^6_eT]^{-1} \quad (52)$$

Where $^6_eT$ is the End Effector Frame in the TCP frame and is expressed as:

$$^6_eT = \begin{bmatrix} I & \begin{bmatrix} a_7 \\ 0 \\ 0 \end{bmatrix} \\ 0 & 1 \end{bmatrix} \quad (53)$$

By substituting the above equations into Equation 31:

$$^6_0T = \begin{bmatrix} \hat{x}_{7'} & \hat{y}_{7'} & \hat{z}_{7'} & \begin{bmatrix} u_0+a_7 \\ v'' \\ w'' \end{bmatrix} \\ 0 & & & 1 \end{bmatrix} \begin{bmatrix} \hat{x}_7 & \hat{y}_7 & \hat{z}_7 & \begin{bmatrix} u'+a_7 \\ v' \\ w' \end{bmatrix} \\ 0 & & & 1 \end{bmatrix}^{-1} \begin{bmatrix} {}^0_eT \begin{bmatrix} I & \begin{bmatrix} a_7 \\ 0 \\ 0 \end{bmatrix} \\ 0 & 1 \end{bmatrix}^{-1} \end{bmatrix}^{-1} \quad (54)$$

Finally, by applying the relative motion between the TCP frame and the Base Frame, the Rotated TCP Frame can be expressed in the Base Frame as:

$$^0_{6'}T = [{}^{6'}_0T]^{-1} \quad (55)$$

Figure 22:
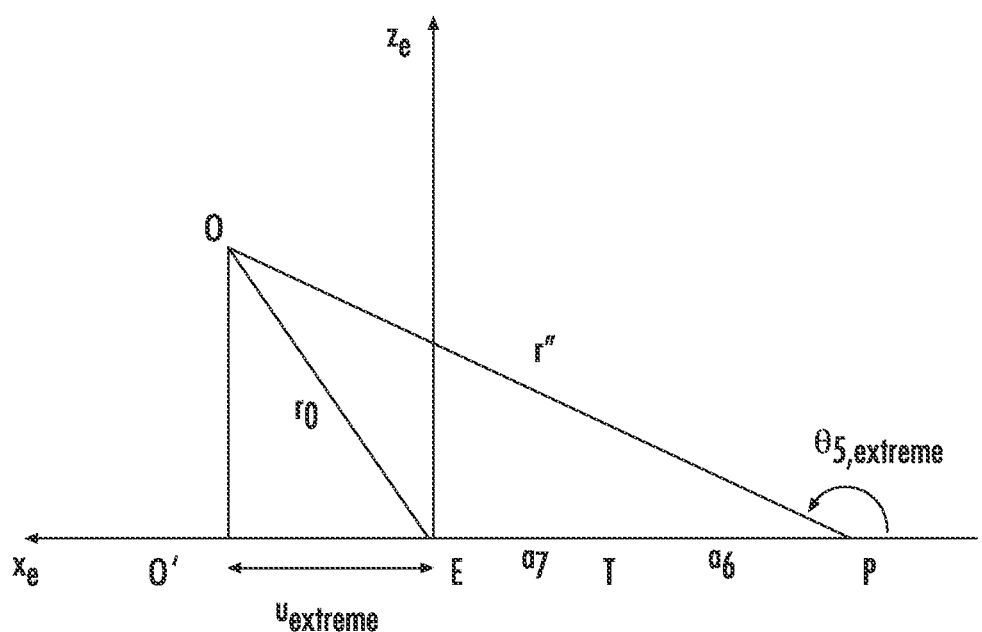
FIG. 22 is a model illustrating detection of an extreme condition for the long jawed instrument of FIG. 17.

With reference to FIG. 22, an extreme condition for the long-jaw instrument is shown such that the distance between the trocar point :O: and the pitch point "P" is:

$$(r'' \cos(\pi - \theta_{5,extreme}) - a_6 - a_7)^2 + (r'' \sin(\pi - \theta_{5,max}))^2 = r_0^2 \quad (56)$$

Solving $r''$ from Equation 56 provides:

$$u_{extreme} = r'' \cos(\pi - \theta_{5,extreme}) - a_6 - a_7 \quad (58)$$

Thus, the steps of the complete inverse kinematics algorithm for a long-jaw instrument are as follows:

1) For each given input pose $^0_6T$, calculate the trocar point "O" position in the End Effector Frame using Equation 42;
2) Use Equation 40 to check if the input pose needs correction, if correction is needed got to step 3, otherwise calculate $^0_6T$ from Equation 52 and go to step 5;
3) Check if $u'>u_{extreme}$ with Equation 57, if true provide feedback, else got to Step 4;
4) Use Equations 49-55 to calculate a corrected pose $^0_{6'}T$, and replace the original pose $^0_6T$ with the corrected pose $^0_{6'}T$;
5) Reapply Equations 3-18 to calculate the joint angles $\theta_1$, $\theta_2$, $\theta_3$, $\theta_5$, and $\theta_6$ as well as the distance $d_4$.

It is also within the scope of this disclosure to provide a clinician with an indication or an alert when the arm 12 and the tool 20 are approaching a singularity or may experience reduced DOF. Thus, while checking whether $u'>u_{extreme}$, if the angle approaches the extreme angle $\theta_{extreme}$ (e.g., $\pi/6$ or 30°), then the $\hat{x}_6$ axis may be pointing back to the trocar point "O" such that the motion of the $\hat{x}_6$ axis will be significantly amplified. In such a condition, the inverse kinematic solution may become less stable and the algorithm may provide a warning to the user such that mapping between the input handle 43 (FIG. 1) and the tool 20 (FIG. 1) may be decoupled until the pose is corrected in Step 4 of the algorithm detailed above.

Referring briefly back to FIG. 12, when the input pose $^0_{6'}T$ positions the trocar point "O" on the left side of the boundary line "B" the tool 20 would be functioning in an undesired configuration (e.g., with a possible decrease in DOF or the desired pose of the tool 20 may not be reachable in light of the current pose of the arm 12 or the desired pose of the tool 20 may be close to a singularity). In response to such an input pose, it may be desirable to correct the pose of the arm 12 using the projection method, as detailed above.

During a medical procedure, when a correction of the pose of the arm 12 is desirable, the user interface 40 (FIG. 1) may provide feedback to a clinician interfacing with the input handles 42. The feedback may be visual, audible, or haptic. One form of haptic feedback is force feedback that may inform the clinician of the current status of the configuration of the arm 12 and the tool 20. The force feedback would provide a tactile force through the input handle 42 as the boundary line "B" is approached and/or crossed. For example, the tactile force may have a first feedback force as the boundary line B is approached and a second stronger feedback force as the boundary line "B" is crossed. The feedback forces can be generated by a feedback torque of a force feedback system (not explicitly shown). With reference to FIG. 15, the feedback torque can be expressed in the Base Frame as:

$$\hat{\tau} = f(\phi) \vec{T}M \times \vec{T}O / |\vec{T}M \times \vec{T}O| \quad (59)$$

In Equation 42, $f(\phi)$ is a scalar function that determines the magnitude of the feedback torque $\hat{t}$ and the cross product of $\vec{T}M$ and $\vec{T}O$ determines the direction of the feedback torque $\hat{t}$. The $f(\phi)$ may be a linear function or may be an exponential function that is limited by a maximum torque. The maximum torque may be set by torque that is realizable by the force feedback system and/or may be set by torque that is physiologically meaningful to a clinician interfacing with the input handles 42. It will be appreciated that in Equation 42 the feedback torque $\hat{t}$ is expressed in the Base Frame and that when displayed or applied by the input handles 42 of the user interface 40, the feedback torque $\hat{t}$ would be expressed in the proper frame of the user interface 40.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A robotic surgical system comprising:
   a user interface including an input handle movable to output an input pose having an input angle;
   a robotic arm including a surgical instrument, wherein the surgical instrument includes:
     a shaft;
     a link coupled to the shaft and pivotal relative to the shaft at a pitch angle about a pitch point; and
     a tool coupled to the link and pivotal relative to the link at a yaw angle about a yaw axis having a tool center point; and
   a processing unit configured to:
     receive the input pose;
     calculate an inverse kinematic solution for the surgical instrument based on the input pose and a model of the surgical instrument;
     determine whether the inverse kinematic solution is desirable based on at least one of joint limit, speed limit, or an acceleration limit of the surgical instrument;
     correct the input pose based on the inverse kinematic solution being undesirable;
     recalculate the inverse kinematic solution for the surgical instrument based on the corrected input pose; and
     command the robotic arm to move the surgical instrument based on the recalculated inverse kinematic solution.

2. The robotic surgical system according to claim 1, further comprising a trocar configured to be inserted into a patient at a trocar point to allow passage of the surgical instrument therethrough.

3. The robotic surgical system according to claim 2, wherein the input angle exceeds at least one of the pitch angle or the yaw angle.

4. The robotic surgical system according to claim 2, wherein the trocar point and the pitch point define a pitch plane.

5. The robotic surgical system according to claim 4, wherein the pitch point and the tool center point define a yaw plane.

6. The robotic surgical system according to claim 5, wherein the processing unit is further configured to define the yaw angle and to calculate the inverse kinematic solution based on the yaw angle.

7. The robotic surgical system according to claim 5, wherein the processing unit is further configured to determine whether the pitch plane is uniquely defined and intersects the yaw plane.

8. The robotic surgical system according to claim 7, wherein the processing unit is further configured to calculate the inverse kinematic solutions based on the determination whether the pitch plane is uniquely defined and intersects the yaw plane.

9. The robotic surgical system according to claim 2, wherein in determining whether the inverse kinematic solution is desirable, the processing unit is further configured to:
   calculate a spherical surface representing a travel path of the trocar point relative to the tool center point;
   define a boundary plane separating the spherical surface; and
   determine whether the inverse kinematic solution is desirable based on a position of the trocar point relative to the boundary.

10. The robotic surgical system according to claim 9, wherein in correcting of the input pose, the processing unit is further configured to:
    project the trocar point onto the boundary plane to generate a projected point; and
    rotate the input pose to the projected point to generate the corrected input pose.

11. A method for controlling a robotic surgical system, the method comprising:
    receiving an input pose at a processing unit from a user interface including an input handle movable to output the input pose;
    calculating an inverse kinematic solution for a surgical instrument coupled to and movable by a robotic arm based on the input pose and a model of the surgical instrument including:
      a shaft;
      a link coupled to the shaft and pivotal relative to the shaft at a pitch angle about a pitch point; and
      a tool coupled to the link and pivotal relative to the link at a yaw angle about a yaw axis having a tool center point;

determining whether the inverse kinematic solution is desirable based on at least one of joint limit, speed limit, or an acceleration limit of the surgical instrument;

correcting the input pose based on the inverse kinematic solution being undesirable;

recalculating the inverse kinematic solution for the surgical instrument based on the corrected input pose; and commanding the robotic arm to move the surgical instrument based on the recalculated inverse kinematic solution.

12. The method according to claim 11, wherein the surgical instrument is movable by a robotic arm based on the input pose while the instrument is inserted into a trocar that is inserted into a patient at a trocar point to allow passage of the surgical instrument therethrough.

13. The method according to claim 12, wherein determining whether the kinematic solution is desirable, further includes:

calculating a spherical surface representing a travel path of the trocar point relative to the tool center point;

defining a boundary plane separating the spherical surface; and determining whether the inverse kinematic solution is desirable based on a position of the trocar point relative to the boundary.

14. The method according to claim 13, wherein correcting the input pose, further includes:

projecting the trocar point onto the boundary plane to generate a projected point; and rotating the input pose to the projected point to generate the corrected input pose.

15. A method for controlling a robotic surgical system, the method comprising:

receiving an input pose at a processing unit from a user interface including an input handle movable to output the input pose;

calculating an inverse kinematic solution for a surgical instrument having a tool center point, the surgical instrument coupled to and movable by a robotic arm based on the input pose while the instrument is inserted into a trocar that is inserted into a patient at a trocar point to allow passage of the surgical instrument therethrough;

determining whether the inverse kinematic solution is desirable based on at least one of joint limit, speed limit, or an acceleration limit of the surgical instrument;

calculating a spherical surface representing a travel path of the trocar point relative to the tool center point;

defining a boundary plane separating the spherical surface;

determining whether the inverse kinematic solution is desirable based on a position of the trocar point relative to the boundary; and commanding the robotic arm to move the surgical instrument based on the inverse kinematic solution.

16. The method according to claim 15, further comprising:

correcting the input pose based on the inverse kinematic solution being undesirable;

recalculating the inverse kinematic solution for the surgical instrument based on the corrected input pose; and commanding the robotic arm to move the surgical instrument based on the recalculated inverse kinematic solution.

* * * * *